(12) United States Patent
Komiyama et al.

(10) Patent No.: US 8,952,174 B2
(45) Date of Patent: *Feb. 10, 2015

(54) PROCESS FOR PRODUCING PHENYL-SUBSTITUTED HETEROCYCLIC DERIVATIVE THROUGH COUPLING USING TRANSITION METAL CATALYST

(75) Inventors: Masato Komiyama, Hino (JP); Naoki Yajima, Hino (JP); Masayuki Kurokawa, Hino (JP)

(73) Assignee: Teijin Pharma Limited, Tokyo (JP)

( * ) Notice: Subject to any disclaimer, the term of this patent is extended or adjusted under 35 U.S.C. 154(b) by 647 days.

This patent is subject to a terminal disclaimer.

(21) Appl. No.: 13/148,820

(22) PCT Filed: Feb. 26, 2010

(86) PCT No.: PCT/JP2010/053043
§ 371 (c)(1),
(2), (4) Date: Aug. 10, 2011

(87) PCT Pub. No.: WO2010/098428
PCT Pub. Date: Sep. 2, 2010

(65) Prior Publication Data
US 2011/0313169 A1 Dec. 22, 2011

(30) Foreign Application Priority Data

Feb. 27, 2009 (JP) .................. 2009-046003
Jun. 29, 2009 (JP) .................. 2009-153770

(51) Int. Cl.
*C07D 277/56* (2006.01)
*C07D 277/20* (2006.01)

(52) U.S. Cl.
CPC ............ *C07D 277/20* (2013.01); *C07D 277/56* (2013.01)
USPC ........................................... 548/201

(58) Field of Classification Search
None
See application file for complete search history.

(56) References Cited

U.S. PATENT DOCUMENTS

| 8,067,446 B2 * | 11/2011 | Kawakami et al. ........... 514/354 |
| 8,426,453 B2 | 4/2013 | Kawakami et al. |
| 2009/0036428 A1 | 2/2009 | Kawakami et al. |

FOREIGN PATENT DOCUMENTS

| EP | 1783116 | 5/2007 |
| EP | 1932832 | 6/2008 |
| EP | 1992361 | 11/2008 |
| JP | 2012096999 | 5/2012 |
| WO | 2007/097403 A1 | 8/2007 |
| WO | 2012026565 | 3/2012 |

OTHER PUBLICATIONS

Roger et al., "Ligand-Free Palladium-Catalyzed Direct Arylation of Thiazoles at Low Catalyst Loadings", J. Org. Chem., 74:1179-1186 (2009).
European Communication dated Jul. 16, 2012, with Supplementary European Search Report dated Jul. 10, 2012, for EP Application No. 10746307.
Turner et al., "Direct Arylation of Thiazoles on Water", Angeu. Chem., 119:8142-8146 (2007).
L. Campeau, et al., "Catalytic Direct Arylation with Aryl Chlorides, Bromides, and Iodines: Intramolecular Studies Leading to New Intermolecular Reactions," J. Am. Chem. Soc., 2006, pp. 581-590, vol. 128.
J. Canivet, "Nickel-Catalyzed Biaryl Coupling of Heteroarenes and Aryl Halides/Triflates," American Chemical Society, Organic Letters, 2009, pp. 1733-1736, vol. 11, No. 8.
H. Do, et al., "Copper-Catalyzed Arylation of Heterocycle C-H Bonds," J. Am. Chem. Soc., 2007, pp. 12404-12405, vol. 129.
M. LaFrance, et al., "Palladium-Catalyzed Benzene Arylation: Incorporation of Catalytic Pivalic Acid as a Proton Shuttle and a Key Element in Catalyst Design," J. Am. Chem. Soc., 2006, pp. 16496-16497, vol. 128.
A. Mori, et al., "Facile Synthesis of 2,5-Diarylthiazoles via Palladium-Catalyzed Tandem C-H Substitutions, Design of Tunable Light Emission and Liquid Crystalline Characteristics," J. Am. Chem. Soc., 2003, pp. 1700-1701, vol. 125.
G.L. Turner, et al., "Direct Arylation of Thiazoles on Water," Angewandte Chem. Int. Ed., 2007, pp. 7996-8000, vol. 46.
International Search Report of PCT/JP2010/053043 dated Apr. 20, 2010.
Communication for EP Application No. 14163761.1 dated Jun. 10, 2014, with European Search Report (dated Jun. 2, 2014).
Berman et al., "Rh(I)-Catalyzed direct arylation of pyridines and quinolines", Journal of the American Chemical Society, 130(45):14926-14927 (2008).
Mukhopadhyay et al., "Regiospecific cross-coupling of haloaryls and pyridine to 2-phenylpyridine using water, zinc, and catalytic palladium on carbon", Journal of the Chemical Society, Perkin Transactions 2, 9:1809-1812 (2000).
Liégualt et al., "Establishment of broadly applicable reaction conditions for the palladium-catalyzed direct arylation of heteroatom-containing aromatic compounds", The Journal of Organic Chemistry, 74(5):1826-1834 (2009).

* cited by examiner

*Primary Examiner* — Kamal Saeed
(74) *Attorney, Agent, or Firm* — Sughrue Mion, PLLC

(57) ABSTRACT

A process for efficiently producing, through few steps either a xanthine oxidase inhibitor, which is a therapeutic agent for hyperuricemia, or an intermediate therefore. The process is a novel coupling process which comprises subjecting a compound represented by formula (1) to coupling reaction with a compound represented by formula (2) in the presence of a transition metal compound to thereby obtain a compound represented by formula (3).

19 Claims, No Drawings

PROCESS FOR PRODUCING PHENYL-SUBSTITUTED HETEROCYCLIC DERIVATIVE THROUGH COUPLING USING TRANSITION METAL CATALYST

CROSS REFERENCE TO RELATED APPLICATIONS

This application is a National Stage of International Application No. PCT/JP2010/053043 filed Feb. 26, 2010 claiming priority based on Japanese Patent Application No. 2009-046003 filed Feb. 27, 2009 and Japanese Application No. 2009-153770 filed Jun. 29, 2009, the contents of all of which are incorporated herein by reference in their entirety.

TECHNICAL FIELD

The present invention relates to a process for producing a phenyl-substituted heterocyclic derivative by using a novel coupling process between a phenyl derivative and a heterocyclic derivative by the use of a transition metal catalyst. More particularly, the present invention relates to an excellent process for producing a phenyl-substituted heterocyclic derivative or an intermediate thereof, which is useful, for example, as a xanthine oxidase inhibitor used as a therapeutic agent for gout, hyperuricemia, and the like.

BACKGROUND ART

The underlying condition of gout is hyperuricemia and, after remission of the gout attack, remedies to improve hyperuricemia are carried out. The therapeutic agents for hyperuricemia are broadly divided into a uricosuric agent and uric acid synthesis inhibitor (xanthine oxidase inhibitor), and are selected appropriately depending on the state and degree of the condition.

The xanthine oxidase (XOD) inhibitors include 2-phenylthiazole derivatives (PTLs 1 to 6, NPL 1), 3-phenylisothiazole derivatives (PTLs 7 and 8), phenylpyrazole derivatives (PTL 9 to 11), 2-phenyloxazole derivatives (PTL 12), and phenyl-heteroaryl derivatives (PTL 13). The production processes described in the patent literatures cited in PTLs 1 to 12 are those wherein heterocyclic rings are formed by production processes comprising a series of consecutive reactions and, thus, involve a large number of steps. The production process described in PTL 13 is a process wherein the skeleton is formed by direct coupling of a phenyl ring with a heterocyclic ring and, thus, involves a small number of steps. However, in this process, it is necessary to prepare boron compounds and therefore results in a higher cost. Thus, this process is not yet satisfactory from a standpoint of a low-cost production process involving a small number of steps.

As a process to bind a C—H bond on a heterocyclic ring directly to a phenyl ring without the use of boron compounds, there have been reported coupling reactions by using, as a catalyst, palladium (NPLs 2 to 10), rhodium (NPL 11), iridium (NPL 12), copper (NPL 13), nickel (NPL 14 and 15), cobalt (NPL 16), palladium-copper (NPL 17 to 19), and palladium-silver (NPL 20). Among them, the production process using a nickel catalyst is related to a synthetic process for a phenyl-substituted heterocyclic derivative which is a xanthine oxidase (XOD) inhibitor (NPL 9). However, there has been reported no example where a phenyl-substituted heterocyclic derivative of the present invention was synthesized by using a metal catalyst other than the nickel catalyst. In addition, none of the reactions is satisfactory from a standpoint of substrate restriction, cost, and yield.

CITATION LIST

Patent Literature

[PTL 1] International Publication No. WO 92/09279
[PTL 2] Japanese Patent Laid-Open Publication No. H6-293746
[PTL 3] Japanese Patent Laid-Open Publication No. H6-329647
[PTL 4] Japanese Patent Laid-Open Publication No. H6-345724
[PTL 5] Japanese Patent Laid-Open Publication No. H10-139770
[PTL 6] Japanese Patent Laid-Open Publication No. H11-60552
[PTL 7] Japanese Patent Laid-Open Publication No. S57-85379
[PTL 8] Japanese Patent Laid-Open Publication No. H6-211815
[PTL 9] Japanese Patent Laid-Open Publication No. S59-95272
[PTL 10] International Publication No. WO 98/18765
[PTL 11] Japanese Patent Laid-Open Publication No. H10-310578
[PTL 12] Japanese Patent Laid-Open Publication No. H6-65210
[PTL 13] International Publication No. WO 2007/097403

Non Patent Literature

[NPL 1] Heterocycles, 1998:47, 857
[NPL 2] J. Am. Chem. Soc., 2003:125, 1700
[NPL 3] J. Am. Chem. Soc., 2006:128, 16496
[NPL 4] Angew. Chem., Int. Ed. 2007:46, 7996
[NPL 5] J. Org. Chem., 2009:74, 1826
[NPL 6] Org. Lett., 2009:10(13), 2909
[NPL 7] Tetrahedron Letters, 2008:49(6), 1045
[NPL 8] Tetrahedron Letters, 2003:59(30), 5685
[NPL 9] Bull. Chem. Soc. Jpn., 1998:71, 467
[NPL 10] Chem. A. Eur. J., 2009:15(6), 1337
[NPL 11] J. Am. Chem. Soc., 2008:130, 14926
[NPL 12] Chem. Comm., 2004, 1926
[NPL 13] J. Am. Chem. Soc., 2007:129(41), 12404
[NPL 14] Org. Lett., 2009:11(8), 1733
[NPL 15] Org. Lett., 2009:11(8), 1737
[NPL 16] Org. Lett., 2003:5(20), 3607
[NPL 17] Tetrahedron, 2007:63(9), 1970
[NPL 18] Org. Lett., 2004:6(12), 2011
[NPL 19] J. Am. Chem. Soc., 2003:125, 1700
[NPL 20] Angew. Chem. Int. Ed., 2007:46, 7996

SUMMARY OF INVENTION

Technical Problem

It is an object of the present invention proposes to provide an excellent short-step production process, which is different from the heretofore known production processes mentioned above, for a phenyl-substituted heterocyclic derivative or its intermediate, the derivative being a xanthine oxidase inhibitor used as a therapeutic agent for gout, hyperuricemia, and the like.

Solution to Problem

The present inventors conducted a diligent research with the above object and, as a result, found that the phenyl ring of a phenyl derivative and a C—H bond on a heterocyclic derivative can be coupled directly with high selectivity by use of a transition metal compound.

That is, the present invention relates to the following:

[1] A process comprising reacting a compound represented by the following formula (1):

[Formula 1]

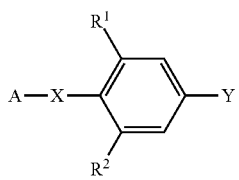
(1)

(In the formula (1), $R^1$ represents a hydrogen atom or halogen atom; $R^2$ represents a hydrogen atom, cyano group, nitro group, halogen atom, formyl group, or halomethyl group; A represents a hydrogen atom, $C_1$ to $C_8$ alkyl group, $C_3$ to $C_6$ cycloalkyl group, phenyl group, fluorine atom (only when X is a bond), or protecting group for a hydroxyl group (only when X is an oxygen atom), wherein A may be substituted by 1 to 3 substituents, such substituent representing a group selected from the group consisting of a halogen atom, $C_1$ to $C_4$ alkyl group, $C_1$ to $C_4$ alkoxy group, $C_1$ to $C_4$ alkylthio group, $C_3$ to $C_6$ cycloalkyl group, phenyl group, phenoxy group, and pyridyl group; X represents a bond (only when A is a phenyl group or fluorine atom) or oxygen atom; and Y represents a leaving group)
and a compound represented by the following formula (2):

[Formula 2]

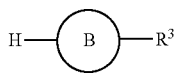
(2)

(In the formula (2), H represents a hydrogen atom; and B represents a group selected from the following formulae:

[Formula 3]

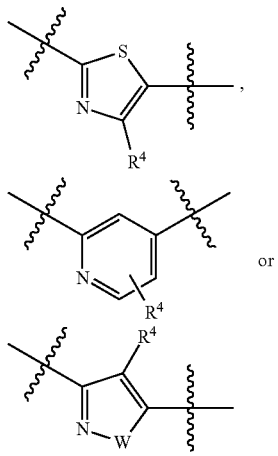
or $R^3$ represents $COOR^{3a}$ or $COR^{3b}$; $R^{3a}$ represents a hydrogen atom, $C_1$ to $C_4$ alkyl group, or ester-type protecting group for a carboxyl group; $R^{3b}$ represents an amide-type protecting group for a carboxyl group, the protecting group forming an amide with a neighboring carbonyl group; $R^4$ represents a hydrogen atom, halogen atom, or $C_1$ to $C_4$ alkyl group; and W represents an oxygen atom or sulfur atom)
in the presence of a transition metal compound to produce a phenyl-substituted heterocyclic derivative represented by the following formula (3):

[Formula 4]

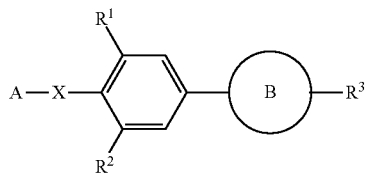
(3)

(in the formula (3), A, X, $R^1$, and $R^2$ are the same as defined in the formula (1); and B and $R^3$ are the same as defined in the formula (2)).

[2] The production process according to [1], wherein A is a $C_1$ to $C_5$ alkyl group.

[3] The production process according to [1], wherein A is an isobutyl group.

[4] The production process according to any of [1] to [3], wherein X is an oxygen atom.

[5] The production process according to any of [1] to [4], wherein $R^1$ is a hydrogen atom.

[6] The production process according to any of [1] to [5], wherein $R^2$ is a cyano group.

[7] The production process according to any of [1] to [6], wherein Y represents a halogen atom, —OCO$_2$—($C_1$ to $C_4$ alkyl group), —OCO$_2$-(phenyl group), —OSO$_2$—($C_1$ to $C_4$ alkyl group), —OSO$_2$-(phenyl group), or a diazonium group, wherein, in Y, the $C_1$ to $C_4$ alkyl group may be substituted with 1 to 3 halogen atoms and the phenyl group may be substituted with 1 to 3 halogen atoms or $C_1$ to $C_4$ alkyl groups.

[8] The production process according to any of [1] to [7], wherein B is represented by the following group:

[Formula 5]

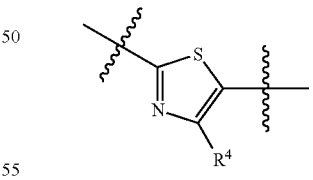

[9] The production process according to any of [1] to [8], wherein $R^4$ is a methyl group.

[10] The production process according to any of [1] to [9], wherein the transition metal compound is zero-valent copper or a salt of mono-valent copper.

[11] The production process according to any of [1] to [9], wherein the transition metal compound is zero-valent palladium or a salt of mono- or di-valent palladium.

[12] The production process according to any of [1] to [9], wherein the transition metal compound is zero-valent palladium or a salt of di-valent palladium.

[13] The production process according to any of [1] to [9], wherein the transition metal compound is zero-valent cobalt or a salt of di-valent cobalt.

[14] The production process according to any of [1] to [9], wherein the transition metal compound is copper (I) iodide (CuI).

[15] The production process according to any of [1] to [9], wherein the transition metal compound is palladium (II) acetate ($Pd(OAc)_2$), palladium (II) propionate ($Pd(O(C=O)CH_2CH_3)_2$), palladium (II) 2-methylpropanoate ($Pd(O(C=O)CH(CH_3)_2)_2$), palladium pivalate ($Pd(OPiv)_2$), palladium (II) chloride ($PdCl_2$), palladium (I) bromide ($Pd_2Br_2$), or palladium (II) hydroxide ($Pd(OH)_2$).

[16] The production process according to any of [1] to [9], wherein the transition metal compound is palladium (II) acetate ($Pd(OAc)_2$), palladium (II) propionate ($Pd(O(C=O)CH_2CH_3)_2$), palladium (II) 2-methylpropanoate ($Pd(O(C=O)CH(CH_3)_2)_2$), or palladium pivalate ($Pd(OPiv)_2$).

[17] The production process according to any of [1] to [9], wherein the transition metal compound is palladium (II) acetate ($Pd(OAc)_2$), palladium (II) chloride ($PdCl_2$), or palladium (II) hydroxide ($Pd(OH)_2$).

[18] The production process according to any of [1] to [9], wherein the transition metal compound is cobalt (II) acetate ($Co(OAc)_2$).

[19] The production process according to any of [1] to [18], wherein a ligand capable of coordinating to the transition metal compound is additionally present during the course of the reaction.

[20] The production process according to [19], wherein the ligand is triphenylphosphine, tri(tert-butyl)phosphine, di(tert-butyl)methylphosphine, tert-butyldicyclohexylphosphine, di(tert-butyl)cyclohexylphosphine, tri(cyclohexyl)phosphine, 2-dicyclohexylphosphino-2',6'-diisopropoxy-1,1'-biphenyl, 2-dicychlohexylphosphino-2',4',6'-triisopropyl-1,1'-biphenyl, phenanthroline, 1,1'-bis(diphenylphosphino)ferrocene, or salts thereof.

[21] The production process according to [19], wherein the ligand is triphenylphosphine, tri(tert-butyl)phosphine, di(tert-butyl)methylphosphine, tert-butyldicyclohexylphosphine, di(tert-butyl)cyclohexylphosphine, tri(cyclohexyl)phosphine, phenanthroline, or 1,1'-bis(diphenylphosphino)ferrocene.

[22] The production process according to [19], wherein the ligand is triphenylphosphine, phenanthroline, or 1,1'-bis(diphenylphosphino)ferrocene.

[23] The production process according to [19], wherein the ligand is a phosphine-type ligand.

[24] The production process according to [23], wherein the ligand is tri(tert-butyl)phosphine, tert-butyldicyclohexylphosphine, di(tert-butyl)methylphosphine, di(tert-butyl)cyclohexylphosphine, tri(cyclohexyl)phosphine, 2-dicyclohexylphosphino-2',6'-diisopropoxy-1,1'-biphenyl, 2-dicyclohexylphosphino-2',4',6'-triisopropyl-1,1'-biphenyl, or a salt thereof.

[25] The production process according to [23], wherein the ligand is tri(tert-butyl)phosphine, tert-butyldicyclohexylphosphine, di(tert-butyl)methylphosphine, di(tert-butyl)cyclohexylphosphine, or tri(cyclohexyl)phosphine.

[26] The production process according to any of [1] to [25], wherein a base is additionally present during the course of the reaction.

[27] The production process according to [26], wherein the base is lithium tert-butoxide.

[28] The production process according to [26], wherein the base is potassium carbonate or cesium carbonate.

[29] The production process according to any of [1] to [28], wherein a silver salt is additionally present during the course of the reaction.

[30] The production process according to [29], wherein the silver salt is silver carbonate.

[31] The production process according to any of [1] to [30], wherein a $C_1$ to $C_{12}$ carboxylic acid or salt thereof is additionally present during the course of the reaction.

[32] The production process according to any of [1] to [30], wherein a $C_1$ to $C_6$ carboxylic acid or a salt thereof is additionally present during the course of the reaction.

[33] The production process according to [32], wherein the carboxylic acid or salt thereof is 2-methylpropanoic acid, pivalic acid, or a salt thereof.

[34] The production process according to [32], wherein the carboxylic acid or a salt thereof is pivalic acid.

Advantageous Effects of Invention

According to the present invention, a phenyl-substituted heterocyclic derivative (a compound represented by the formula (3)) can be obtained in a process involving a small number of steps by subjecting a phenyl derivative (a compound represented by the formula (1)) and a heterocyclic derivative (a compound represented by the formula (2)) to a selective coupling reaction by using a transition metal catalyst.

Furthermore, since the process involves a small number of steps, it is possible to produce the phenyl-substituted heterocyclic derivative (a compound represented by the formula (3)) in high yield and at low cost.

DESCRIPTION OF EMBODIMENTS

The terms used singly or in combination in the present description will be explained in the following. Unless otherwise noted, explanation of each substituent shall be common to each position. In addition, a combination of substituents and variables is allowed only when such a combination results in a chemically stable compound. When the substituent itself is substituted with two or more groups, these many groups can exist on the same or different carbon atom as long as a stable structure is formed.

In the present invention, the "halogen atom" means a fluorine atom, chlorine atom, bromine atom, or iodine atom.

In the present invention, the "$C_1$ to $C_8$ alkyl group" means a linear or branched saturated aliphatic hydrocarbon group having 1 to 8 carbon atoms and includes, for example, a methyl group, ethyl group, n-propyl group, isopropyl group, n-butyl group, isobutyl group, tert-butyl group, n-pentyl group, isopentyl group, neopentyl group, 1-methylpropyl group, n-hexyl group, isohexyl group, 1,1-dimethylbutyl group, 2,2-dimethylbutyl group, 3,3-dimethylbutyl group, n-heptyl group, n-octyl group, and the like.

In the present invention, the "$C_1$ to $C_4$ alkoxy group" means a group consisting of the "$C_1$ to $C_4$ alkyl group" and an oxy group. The examples include a methoxy group, ethoxy group, n-propyloxy group, isopropyloxy group, n-butyloxy group, isobutyloxy group, tert-butyloxy group, and the like.

In the present invention, the "$C_3$ to $C_6$ cycloalkyl group" means a cyclic alkyl group having 3 to 6 carbon atoms and includes, for example, a cyclopropyl group, cyclobutyl group, cyclopentyl group, cyclohexyl group, and the like.

In the present invention, the "$C_1$ to C4 alkylthio group" means a group consisting of the "$C_1$ to $C_4$ alkyl group" and a thio group. The examples include a methylthio group, ethylthio group, n-propylthio group, isopropylthio group, n-butylthio group, isobutylthio group, tert-butylthio group, and the like.

In the present invention, the "halomethyl group" means a methyl group substituted with one or more halogen atoms and includes, for example, a trifluoromethyl group, difluoromethyl group, fluoromethyl group, trichloromethyl group. dichloromethyl group, chloromethyl group, tribromomethyl group, dibromomethyl group, bromomethyl group, and the like.

In the present invention, the "leaving group" means an atom or a group of atoms which departs from the reaction substrate in a substitution reaction, elimination reaction, or the like. Such a leaving group includes, for example, a halogen atom, —OCO$_2$—($C_1$ to $C_4$ alkyl group), —OCO$_2$-(phenyl group), —OSO$_2$—($C_1$ to $C_4$ alkyl group), —OSO$_2$-(phenyl group), diazonium group (–N$^+$≡N), or the like. Furthermore, the $C_1$ to $C_4$ alkyl group and the phenyl group that constitute the leaving group may be substituted with 1 to 3 halogen atoms and with 1 to 3 halogen atoms or $C_1$ to $C_4$ alkyl groups, respectively. However, the present invention is not limited to these.

The "protecting group for a hydroxyl group" means a group which protects the hydroxyl group. Such a "protecting group for a hydroxyl group" is well known in the art and is classified into an ether-type protecting group, silyl ether-type protecting group, ester-type protecting group, carbonate-type protecting group, phosphine-type protecting group, sulfonate-type protecting group, and the like. Examples include the groups described as a protecting group for phenol and the like in T. W. Greene and P. G. M. Wuts, "Protective Groups in Organic Synthesis (3rd Ed., 1994), (4th Ed., 2006)" and the like, such as a benzyloxymethyl group, methoxyethoxymethyl group, phenylthiomethyl group, phenacylmethyl group, 4-bromophenacylmethyl group, cyclopropylmethyl group, allyl group, propargyl group, cyclohexyl group, benzyl group, ortho-nitrobenzyl group, 4-(dimethylamino)carbonylbenzyl group, 4-methylsulfinylbenzyl group, 9-anthranylmethyl group, 4-picoryl group, trimethylsilyl group, tert-butyldimethylsilyl group, tert-butyldiphenylsilyl group, triisopropylsilyl group, formyl group, —(C=O)—($C_1$ to $C_4$ alkyl group), benzoyl group, 4-oxopentanoyl group, pivaloyl group, methyl ester group, 1-adamantyloxycarbonyl group, tert-butoxycarbonyl group, 4-methylsulfinylbenzyloxycarbonyl group, 2,4-dimethylpent-3-yloxycarbonyl group, 2,2,2-trichloroethoxycarbonyl group, vinyloxycarbonyl group, benzyloxycarbonyl group, —(C=O)NH—($C_1$ to $C_4$ alkyl group), methanesulfonyl group, toluenesulfonyl group, and the like. However, the present invention is not limited to the groups exemplified herein and any group may be selected as long as it is used as a protecting group for the hydroxyl group. Here, the protecting group for the hydroxyl group as A is used as such when X is an oxygen atom. For example, when a benzyl group is the protecting group, A-X— corresponds to PhCH$_2$—O—.

The "ester-type protecting group for a carboxyl group" in the present invention means a group which protects the carboxyl group by combining with the oxygen atom of the carboxyl group to be protected and forming an ester. Such an "ester-type protecting group for a carboxyl group" includes the groups described as an ester-type protecting group for the carboxyl group in T. W. Greene and P. G. M. Wuts, "Protective Groups in Organic Synthesis (3rd Ed., 1994), (4th Ed., 2006)," such as a $C_1$ to $C_6$ alkyl group, 9-fluorenylmethyl group, methoxymethyl group, methylthiomethyl group, tetrahydropyranyl group, tetrahydrofuranyl group, methoxyethoxymethyl group, 2-(trimethylsilyl)ethoxymethyl group, benzyloxymethyl group, pivaloyloxymethyl group, phenylacetoxymethyl group, triisopropylsilylmethyl group, para-bromophenacyl group, α-methylphenacyl group, para-methoxyphenacyl group, decyl group, carboxamidomethyl group, para-azobenzenecarboxamidomethyl group, N-phthalimidomethyl group, 2,2,2-trichloroethyl group, 2-haloethyl group, ω-chloroalkyl group, 2-(triethylsilyl)ethyl group, 2-methylthioethyl group, 1,3-dithianyl-2-methyl group, 2-(para-nitrophenylsulfenyl)ethyl group, 2-(para-toluenesulfonyl)ethyl group, 2-(2'-pyridyl)ethyl group, 2-(para-methoxyphenyl)ethyl group, 2-(diphenylphosphino)ethyl group, 1-methyl-1-phenylethyl group, 2-(4-acetyl-2-nitrophenyl)ethyl group, 2-cyanoethyl group, dicyclopropylmethyl group, cyclopentyl group, cyclohexyl group, allyl group, methallyl group, 2-methylbut-3-en-2-yl group, 3-methylbut-2-(prenyl) group, 3-buten-1-yl group, 4-(trimethylsilyl)-2-buten-1-yl group, cinnamyl group, α-methylcinnamyl group, prop-2-ynyl (propargyl) group, phenyl group, 2,6-dimethylphenyl group, 2,6-diisopropylphenyl group, 2,6-di(tert-butyl)-4-methylphenyl group, 2,6-di(tert-butyl)-4-methoxylphenyl group, para-(methylthio)phenyl group, pentafluorophenyl group, benzyl group, triphenylmethyl group, diphenylmethyl group, bis(ortho-nitrophenyl)methyl group, 9-anthranylmethyl group, 2-(9,10-dioxo)anthranylmethyl group, 5-dibenzosuberyl group, 1-pyrenylmethyl group, 2-(trifluoromethyl)-6-chromonylmethyl group, 2,4,6-trimethylbenzyl group, para-bromobenzyl group, ortho-nitrobenzyl group, para-nitrobenzyl group, para-methoxybenzyl group, 2,6-dimethoxybenzyl group, 4-(methylsulfinyl) benzyl group, 4-sulfobenzyl group, 4-azidomethoxybenzyl group, piperonyl group, 4-piconyl group, para-benzyl group, trimethylsilyl group, triethylsilyl group, tert-butyldimethylsilyl group, isopropyldimethylsilyl group, phenyldimethylsilyl group, di(tert-butyl)methylsilyl group, triisopropylsilyl group, $C_1$ to $C_6$ alkylthio group, oxazole group, 2-alkyl-1,3-oxazoline group, 4-alkyl-5-oxo-1,3-oxazolidine group, 2,2-bistrifluoromethyl-4-alkyl-5-oxo-1,3-oxazolidine group, 5-alkyl-4-oxo-1,3-dioxolane group, dioxanone group, and the like. However, the present invention is not limited to the groups exemplified herein and any group may be selected as long as it is used as a protecting group for the carboxyl group.

The "amide-type protecting group for a carboxyl group" in the present invention means a group which protects the carboxyl group by combining with the carbonyl carbon atom of the carboxyl group to be protected and forming an amide. Such an "amide-type protecting group for a carboxyl group" includes the groups described as a protecting group for the carboxyl group in T. W. Greene and P. G. M. Wuts, "Protective Groups in Organic Synthesis (3rd Ed., 1994), (4th Ed., 2006)," such as an N,N-dimethylamino group, pyrrolidinyl group, piperidinyl group, 5,6-dihydrophenanthridyl group, ortho-nitrophenylamino group, N-7-nitroindolyl group, N-8-nitro-1,2,3,4-tetrahydroquinolyl group, N-phenylhydrazyl group, N,N'-diisopropylhydrazyl group, and the like. However, the present invention is not limited to the groups exemplified herein and any amino group may be selected as long as it is used as a protecting group for the carboxyl group.

In the present invention, "C" such as in "$C_1$" and the like represents a carbon atom and the numeral which follows it represents the number of the carbon atoms. For example, "$C_1$ to $C_6$" represents a range of the number of carbon atoms from 1 to 6. Naturally, in the present invention, when the number of carbon atoms is different, the corresponding group is different. For example, a "$C_1$ to $C_4$ alkyl group" means a group having 1 to 4 carbon atoms among the alkyl groups defined by the "$C_1$ to $C_8$ alkyl group." Treatment of the number of carbon atoms in other groups is the same.

The "diazonium group" in the present invention may form a salt. Such a salt includes a fluoride salt, chloride salt, bromide salt, iodide salt, tetrafluoroborate salt, and the like.

Abbreviations used in the present invention are as follows: TfO: trifluoromethanesulfonyloxy group, MsO: methanesulfonyloxy group, TsO: toluenesulfonyloxy group, Me: methyl group, Et: ethyl group, n-Pr: n-propyl group, i-Pr: isopropyl group, i-Bu: isobutyl group, t-Bu: tert-butyl group, MeO: methoxy group, Ph: phenyl group, OAc: acetyloxy group, 4-MeO-Ph: 4-methoxy-phenyl group, Cy: cyclohexyl group, Piv: pivaloyl group.

The present invention relates to a process comprising reacting a compound represented by the following formula (1):

[Formula 6]

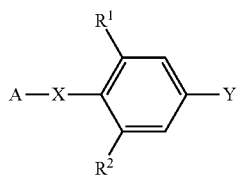

(1)

and a compound represented by the following formula (2):

[Formula 7]

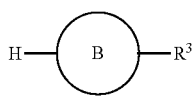

(2)

in the presence of a transition metal compound to produce a phenyl-substituted heterocyclic derivative represented by the following formula (3):

[Formula 8]

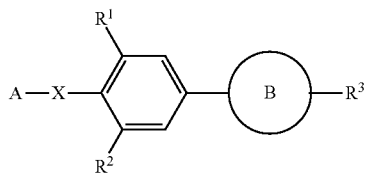

(3)

In the formulae (1) and (3), $R^1$ represents a hydrogen atom or halogen atom.

The "halogen atom" in $R^1$ is preferably a chlorine atom or fluorine atom, more preferably a fluorine atom.

As a whole, $R^1$ is preferably a hydrogen atom.

In the formulae (1) and (3), $R^2$ represents a hydrogen atom, cyano group, nitro group, halogen atom, formyl group, or halomethyl group.

The "halogen atom" in $R^2$ is preferably a bromine atom.

The "halomethyl group" in $R^2$ is preferably a chloromethyl group, dichloromethyl group, trichloromethyl group, or trifluoromethyl group.

As a whole, $R^2$ is preferably a cyano group, nitro group, or formyl group and, above all, a cyano group is preferable.

In the formulae (1) and (3), A represents a hydrogen atom, $C_1$ to $C_8$ alkyl group, $C_3$ to $C_6$ cycloalkyl group, phenyl group, fluorine atom (only when X is a bond), or protecting group for a hydroxyl group (only when X is an oxygen atom). Here, the protecting group for a hydroxyl group as A is used as such when X is an oxygen atom. For example, when the protecting group is a benzyl group, A-X— represents $PhCH_2$—O—.

Furthermore, A may be substituted with 1 to 3 substituents, such substituent representing a group selected from the group consisting of a halogen atom, $C_1$ to $C_4$ alkyl group, $C_1$ to $C_4$ alkoxy group, $C_1$ to $C_4$ alkylthio group, $C_3$ to $C_6$ cycloalkyl group, phenyl group, phenoxy group, and pyridyl group.

The "$C_1$ to $C_8$ alkyl group" in A is preferably a methyl group, ethyl group, n-propyl group, isopropyl group, n-butyl group, isobutyl group, tert-butyl group, n-pentyl group, isopentyl group, or neopentyl group. Above all, preferable is an isobutyl group or neopentyl group; more preferable is an isobutyl group.

As a whole, A is preferably a $C_1$ to $C_5$ alkyl group.

In the formulae (1) and (3), X represents a bond (only when A is a phenyl group or fluorine atom) or an oxygen atom. Above all, an oxygen atom is preferable.

In the formula (1), Y represents a leaving group. Above all, preferable is a halogen atom, —$OCO_2$—($C_1$ to $C_4$ alkyl group), —$OCO_2$-(phenyl group), —$OSO_2$—($C_1$ to $C_4$ alkyl group), —$OSO_2$-(phenyl group), or a diazonium group.

When the leaving group as Y is "—$OCO_2$—($C_1$ to $C_4$ alkyl group)" or "—$OSO_2$—($C_1$ to $C_4$ alkyl group)," such a "$C_1$ to $C_4$ alkyl group" in Y is preferably a methyl group.

When the leaving group as Y is "—$OCO_2$—($C_1$ to $C_4$ alkyl group)" or "—$OSO_2$—($C_1$ to $C_4$ alkyl group)," such a "$C_1$ to $C_4$ alkyl group" in Y may be substituted with 1 to 3 halogen atoms. Such a "halogen atom" is preferably a fluorine atom. It is particularly preferable that the group is substituted with three fluorine atoms.

When the leaving group as Y is "—$OCO_2$-(phenyl group)" or "—$OSO_2$-(phenyl group)," such a "phenyl group" in Y may be substituted with 1 to 3 halogen atoms or $C_1$ to $C_4$ alkyl groups. Such a "$C_1$ to $C_4$ alkyl group" is preferably a methyl group.

When the leaving group as Y is a "halogen atom," the "halogen atom" is preferably an iodine atom, bromine atom, or chlorine atom. Above all, an iodine atom or bromine atom is preferable.

The "diazonium group" may form a salt. When the leaving group as Y represents a "diazonium group," the salt of the "diazonium group" is preferably a tetrafluoroborate.

As a whole, Y is preferably an iodine atom, bromine atom, trifluoromethanesulfonyloxy group, or the like.

In the formula (2), H represents a hydrogen atom.

In the formulae (2) and (3), B represents a group selected from the following formulae. Meanwhile, the bond at the right-hand side of each of the following formulae is for bonding to $R^3$; and the bond at the left-hand side is for bonding to a hydrogen atom in the formula (2) and to a phenyl group in the formula (3):

[Formula 9]

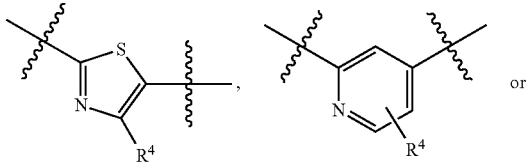

, or

-continued

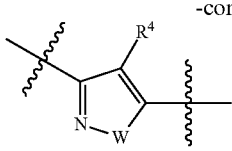

Above all, the following group is preferable:

[Formula 10]

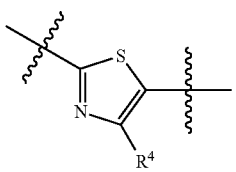

In the formulae (2) and (3), $R^3$ represents $COOR^{3a}$ or $COR^{3b}$.

$R^{3a}$ represents a hydrogen atom, $C_1$ to $C_4$ alkyl group, or ester-type protecting group for a carboxyl group. Here, the ester-type protecting group for a carboxyl group as $R^{3a}$ protects the carboxyl group which $R^{3a}$ substitutes.

As $R^{3a}$, preferable is a hydrogen atom or $C_1$ to $C_4$ alkyl group.

$R^{3b}$ represents an amide-type protecting group for a carboxyl group which forms an amide with a neighboring carbonyl group.

As a whole, $R^3$ is preferably $COOR^{3a}$.

In the formulae (2) and (3), $R^4$ represents a hydrogen atom, halogen atom, or $C_1$ to $C_4$ alkyl group.

The "halogen atom" in $R^4$ is preferably a fluorine atom.

The "$C_1$ to $C_4$ alkyl group" in $R^4$ is preferably a methyl group.

As a whole, $R^4$ is preferably a $C_1$ to $C_4$ alkyl group. Above all, a methyl group is preferable.

In the formulae (2) and (3), W represents an oxygen atom or sulfur atom.

In the formula (3), definition of A, X, $R^1$, and $R^2$ and preferable groups thereof are respectively the same as those in the formula (1); and definition of B and $R^3$ and preferable groups thereof are respectively the same as those in the formula (2).

Specific examples of the compounds represented by the formula (1) and specific examples of the compounds represented by formula (2) are listed in Tables 1 to 4 and Tables 5 to 7, respectively. However, the compounds represented by the formula (1) and formula (3) are not limited to such specific examples.

TABLE 1

(1)

| No. | A | X | $R^1$ | $R^2$ | Y |
|---|---|---|---|---|---|
| 1 | i-Bu | O | H | CN | I |
| 2 | i-Bu | O | H | CN | Br |
| 3 | i-Bu | O | H | CN | Cl |

TABLE 1-continued (1)

| No. | A | X | $R^1$ | $R^2$ | Y |
|---|---|---|---|---|---|
| 4 | i-Bu | O | H | CN | OTf |
| 5 | i-Bu | O | H | CN | OMs |
| 6 | i-Bu | O | H | CN | OTs |
| 7 | i-Bu | O | H | CHO | I |
| 8 | i-Bu | O | H | CHO | Br |
| 9 | i-Bu | O | H | CHO | Cl |
| 10 | i-Bu | O | H | CHO | OTf |
| 11 | i-Bu | O | H | CHO | OMs |
| 12 | i-Bu | O | H | CHO | OTs |
| 13 | i-Bu | O | H | $NO_2$ | I |
| 14 | i-Bu | O | H | $NO_2$ | Br |
| 15 | i-Bu | O | H | $NO_2$ | Cl |
| 16 | i-Bu | O | H | $NO_2$ | OTf |
| 17 | i-Bu | O | H | $NO_2$ | OMs |
| 18 | i-Bu | O | H | $NO_2$ | OTs |
| 19 | i-Bu | O | H | H | I |
| 20 | i-Bu | O | H | H | Br |
| 21 | i-Bu | O | H | H | Cl |
| 22 | i-Bu | O | H | H | OTf |
| 23 | i-Bu | O | H | H | OMs |
| 24 | i-Bu | O | H | H | OTs |
| 25 | i-Bu | O | H | Br | I |
| 26 | i-Bu | O | H | Br | Br |
| 27 | i-Bu | O | H | Br | Cl |
| 28 | i-Bu | O | H | Br | OTf |
| 29 | i-Bu | O | H | Br | OMs |
| 30 | i-Bu | O | H | Br | OTs |
| 31 | $(CH_3)_3CCH_2$ | O | H | CN | I |
| 32 | $(CH_3)_3CCH_2$ | O | H | CN | Br |
| 33 | $(CH_3)_3CCH_2$ | O | H | CN | Cl |
| 34 | $(CH_3)_3CCH_2$ | O | H | CN | OTf |
| 35 | $(CH_3)_3CCH_2$ | O | H | CN | OMs |
| 36 | $(CH_3)_3CCH_2$ | O | H | CN | OTs |
| 37 | $(CH_3)_3CCH_2$ | O | H | CHO | I |
| 38 | $(CH_3)_3CCH_2$ | O | H | CHO | Br |
| 39 | $(CH_3)_3CCH_2$ | O | H | CHO | Cl |
| 40 | $(CH_3)_3CCH_2$ | O | H | CHO | OTf |
| 41 | $(CH_3)_3CCH_2$ | O | H | CHO | OMs |
| 42 | $(CH_3)_3CCH_2$ | O | H | CHO | OTs |

TABLE 2

(1)

| No. | A | X | $R^1$ | $R^2$ | Y |
|---|---|---|---|---|---|
| 43 | $(CH_3)_3CCH_2$ | O | H | $NO_2$ | I |
| 44 | $(CH_3)_3CCH_2$ | O | H | $NO_2$ | Br |
| 45 | $(CH_3)_3CCH_2$ | O | H | $NO_2$ | Cl |
| 46 | $(CH_3)_3CCH_2$ | O | H | $NO_2$ | OTf |
| 47 | $(CH_3)_3CCH_2$ | O | H | $NO_2$ | OMs |
| 48 | $(CH_3)_3CCH_2$ | O | H | $NO_2$ | OTs |
| 49 | $(CH_3)_3CCH_2$ | O | H | H | I |
| 50 | $(CH_3)_3CCH_2$ | O | H | H | Br |
| 51 | $(CH_3)_3CCH_2$ | O | H | H | Cl |
| 52 | $(CH_3)_3CCH_2$ | O | H | H | OTf |
| 53 | $(CH_3)_3CCH_2$ | O | H | H | OMs |

TABLE 2-continued

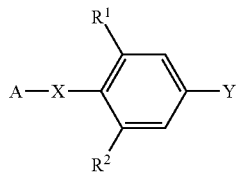
(1)

| No. | A | X | R¹ | R² | Y |
|---|---|---|---|---|---|
| 54 | $(CH_3)_3CCH_2$ | O | H | H | OTs |
| 55 | $(CH_3)_3CCH_2$ | O | H | Br | I |
| 56 | $(CH_3)_3CCH_2$ | O | H | Br | Br |
| 57 | $(CH_3)_3CCH_2$ | O | H | Br | Cl |
| 58 | $(CH_3)_3CCH_2$ | O | H | Br | OTf |
| 59 | $(CH_3)_3CCH_2$ | O | H | Br | OMs |
| 60 | $(CH_3)_3CCH_2$ | O | H | Br | OTs |
| 61 | Benzyl | O | H | CN | I |
| 62 | Benzyl | O | H | CN | Br |
| 63 | Benzyl | O | H | CN | Cl |
| 64 | Benzyl | O | H | CN | OTf |
| 65 | Benzyl | O | H | CN | OMs |
| 66 | Benzyl | O | H | CN | OTs |
| 67 | Benzyl | O | H | CHO | I |
| 68 | Benzyl | O | H | CHO | Br |
| 69 | Benzyl | O | H | CHO | Cl |
| 70 | Benzyl | O | H | CHO | OTf |
| 71 | Benzyl | O | H | CHO | OMs |
| 72 | Benzyl | O | H | CHO | OTs |
| 73 | Benzyl | O | H | $NO_2$ | I |
| 74 | Benzyl | O | H | $NO_2$ | Br |
| 75 | Benzyl | O | H | $NO_2$ | Cl |
| 76 | Benzyl | O | H | $NO_2$ | OTf |
| 77 | Benzyl | O | H | $NO_2$ | OMs |
| 78 | Benzyl | O | H | $NO_2$ | OTs |
| 79 | Benzyl | O | H | H | I |
| 80 | Benzyl | O | H | H | Br |
| 81 | Benzyl | O | H | H | Cl |
| 82 | Benzyl | O | H | H | OTf |
| 83 | Benzyl | O | H | H | OMs |
| 84 | Benzyl | O | H | H | OTs |

TABLE 3

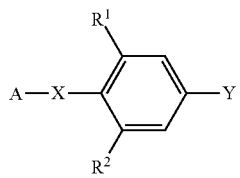
(1)

| No. | A | X | R¹ | R² | Y |
|---|---|---|---|---|---|
| 85 | Benzyl | O | H | Br | I |
| 86 | Benzyl | O | H | Br | Br |
| 87 | Benzyl | O | H | Br | Cl |
| 88 | Benzyl | O | H | Br | OTf |
| 89 | Benzyl | O | H | Br | OMs |
| 90 | Benzyl | O | H | Br | OTs |
| 91 | Ph | bond | H | CN | I |
| 92 | Ph | bond | H | CN | Br |
| 93 | Ph | bond | H | CN | Cl |
| 94 | Ph | bond | H | CN | OTf |
| 95 | Ph | bond | H | CN | OMs |
| 96 | Ph | bond | H | CN | OTs |
| 97 | Ph | bond | H | CHO | I |
| 98 | Ph | bond | H | CHO | Br |
| 99 | Ph | bond | H | CHO | Cl |
| 100 | Ph | bond | H | CHO | OTf |
| 101 | Ph | bond | H | CHO | OMs |
| 102 | Ph | bond | H | CHO | OTs |
| 103 | Ph | bond | H | $NO_2$ | I |

TABLE 3-continued

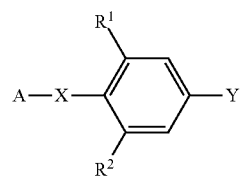
(1)

| No. | A | X | R¹ | R² | Y |
|---|---|---|---|---|---|
| 104 | Ph | bond | H | $NO_2$ | Br |
| 105 | Ph | bond | H | $NO_2$ | Cl |
| 106 | Ph | bond | H | $NO_2$ | OTf |
| 107 | Ph | bond | H | $NO_2$ | OMs |
| 108 | Ph | bond | H | $NO_2$ | OTs |
| 109 | Ph | bond | H | H | I |
| 110 | Ph | bond | H | H | Br |
| 111 | Ph | bond | H | H | Cl |
| 112 | Ph | bond | H | H | OTf |
| 113 | Ph | bond | H | H | OMs |
| 114 | Ph | bond | H | H | OTs |
| 115 | Ph | bond | H | Br | I |
| 116 | Ph | bond | H | Br | Br |
| 117 | Ph | bond | H | Br | Cl |
| 118 | Ph | bond | H | Br | OTf |
| 119 | Ph | bond | H | Br | OMs |
| 120 | Ph | bond | H | Br | OTs |
| 121 | 4-MeO—Ph | bond | H | CN | I |
| 122 | 4-MeO—Ph | bond | H | CN | Br |
| 123 | 4-MeO—Ph | bond | H | CN | Cl |
| 124 | 4-MeO—Ph | bond | H | CN | OTf |
| 125 | 4-MeO—Ph | bond | H | CN | OMs |
| 126 | 4-MeO—Ph | bond | H | CN | OTs |

TABLE 4

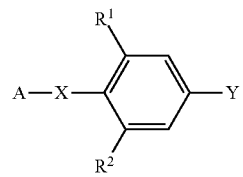
(1)

| No. | A | X | R¹ | R² | Y |
|---|---|---|---|---|---|
| 127 | 4-MeO—Ph | bond | H | CHO | I |
| 128 | 4-MeO—Ph | bond | H | CHO | Br |
| 129 | 4-MeO—Ph | bond | H | CHO | Cl |
| 130 | 4-MeO—Ph | bond | H | CHO | OTf |
| 131 | 4-MeO—Ph | bond | H | CHO | OMs |
| 132 | 4-MeO—Ph | bond | H | CHO | OTs |
| 133 | 4-MeO—Ph | bond | H | $NO_2$ | I |
| 134 | 4-MeO—Ph | bond | H | $NO_2$ | Br |
| 135 | 4-MeO—Ph | bond | H | $NO_2$ | Cl |
| 136 | 4-MeO—Ph | bond | H | $NO_2$ | OTf |
| 137 | 4-MeO—Ph | bond | H | $NO_2$ | OMs |
| 138 | 4-MeO—Ph | bond | H | $NO_2$ | OTs |
| 139 | 4-MeO—Ph | bond | H | H | I |
| 140 | 4-MeO—Ph | bond | H | H | Br |
| 141 | 4-MeO—Ph | bond | H | H | Cl |
| 142 | 4-MeO—Ph | bond | H | H | OTf |
| 143 | 4-MeO—Ph | bond | H | H | OMs |
| 144 | 4-MeO—Ph | bond | H | H | OTs |
| 145 | 4-MeO—Ph | bond | H | Br | I |
| 146 | 4-MeO—Ph | bond | H | Br | Br |
| 147 | 4-MeO—Ph | bond | H | Br | Cl |
| 148 | 4-MeO—Ph | bond | H | Br | OTf |
| 149 | 4-MeO—Ph | bond | H | Br | OMs |
| 150 | 4-MeO—Ph | bond | H | Br | OTs |

TABLE 5

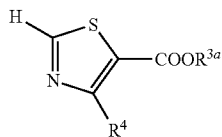

| No. | $R^{3a}$ | $R^4$ |
|---|---|---|
| 151 | t-Bu | $CH_3$ |
| 152 | n-Pr | $CH_3$ |
| 153 | i-Pr | $CH_3$ |
| 154 | Et | $CH_3$ |
| 155 | Me | $CH_3$ |
| 156 | H | $CH_3$ |
| 157 | t-Bu | H |
| 158 | n-Pr | H |
| 159 | i-Pr | H |
| 160 | Et | H |
| 161 | Me | H |
| 162 | H | H |

TABLE 6

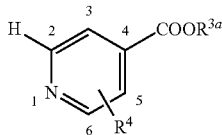

| No. | $R^{3a}$ | $R^4$ |
|---|---|---|
| 163 | t-Bu | 5-$CH_3$ |
| 164 | n-Pr | 5-$CH_3$ |
| 165 | i-Pr | 5-$CH_3$ |
| 166 | Et | 5-$CH_3$ |
| 167 | Me | 5-$CH_3$ |
| 168 | H | 5-$CH_3$ |
| 169 | t-Bu | H |
| 170 | n-Pr | H |
| 171 | i-Pr | H |
| 172 | Et | H |
| 173 | Me | H |
| 174 | H | H |
| 175 | t-Bu | 3-F |
| 176 | n-Pr | 3-F |
| 177 | i-Pr | 3-F |
| 178 | Et | 3-F |
| 179 | Me | 3-F |
| 180 | H | 3-F |
| 181 | t-Bu | 5-Cl |
| 182 | n-Pr | 5-Cl |
| 183 | i-Pr | 5-Cl |
| 184 | Et | 5-Cl |
| 185 | Me | 5-Cl |
| 186 | H | 5-Cl |

TABLE 7

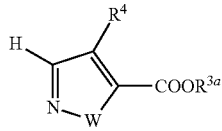

| No. | W | $R^{3a}$ | $R^4$ |
|---|---|---|---|
| 187 | O | t-Bu | $CH_3$ |
| 188 | O | n-Pr | $CH_3$ |
| 189 | O | i-Pr | $CH_3$ |
| 190 | O | Et | $CH_3$ |
| 191 | O | Me | $CH_3$ |

TABLE 7-continued

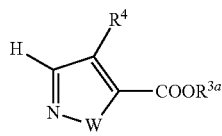

| No. | W | $R^{3a}$ | $R^4$ |
|---|---|---|---|
| 192 | O | H | $CH_3$ |
| 193 | O | t-Bu | H |
| 194 | O | n-Pr | H |
| 195 | O | i-Pr | H |
| 196 | O | Et | H |
| 197 | O | Me | H |
| 198 | O | H | H |
| 199 | S | t-Bu | $CH_3$ |
| 200 | S | n-Pr | $CH_3$ |
| 201 | S | i-Pr | $CH_3$ |
| 202 | S | Et | $CH_3$ |
| 203 | S | Me | $CH_3$ |
| 204 | S | H | $CH_3$ |
| 205 | S | t-Bu | H |
| 206 | S | n-Pr | H |
| 207 | S | i-Pr | H |
| 208 | S | Et | H |
| 209 | S | Me | H |
| 210 | S | H | H |

The production process of the present invention is characterized in that a transition metal compound is used as the catalyst. In the production process of the present invention, the transition metals in the transition metal compounds used are those other than nickel and include copper, palladium, cobalt, iron, rhodium, ruthenium, iridium, and the like. Above all, copper, palladium, or cobalt is preferable. Copper includes zero-valent Cu(0), mono-valent Cu(I), and di-valent Cu(II), wherein preferable is zero-valent Cu(0) or mono-valent Cu(I). Palladium is preferably zero-valent Pd(0), mono-valent Pd(I), or di-valent Pd(II). Cobalt includes zero-valent Co(0), mono-valent Co(I), di-valent Co(II), and tri-valent Co(III), wherein preferable is zero-valent Co(0), mono-valent Co or di-valent Co (II). Iron includes zero-valent Fe(0), di-valent Fe(II), and tri-valent Fe(III), wherein preferable is di-valent Fe(II) or trivalent Fe(III). Rhodium is preferably zero-valent Rh(0) or mono-valent Rh(I). Ruthenium is preferably zero-valent Ru(0) or di-valent Rh(II). Iridium includes zero-valent Ir(0), mono-valent Ir(I), di-valent Ir(II), tri-valent Ir(III), and tetra-valent Ir(IV), wherein preferable is trivalent Ir(III).

The salt of Cu(I) includes copper(I) chloride, copper(I) bromide, copper(I) iodide, copper(I) acetate, copper tetrafluoroborate, copper thiophene-2-carboxylate, hydrates thereof, mixtures of these, and the like.

The salt of Cu(II) includes copper(II) fluoride, copper(II) chloride, copper(II) bromide, copper(II) iodide, copper(II) acetate, copper(II) formate, copper(II) hydroxide, copper(II) nitrate, copper(II) carbonate, copper(II) acetylacetonate, copper(II) borate, copper(II) oxalate, copper(II) phthalate, copper(II) tartrate, copper (II) trifluoromethanesulfonate, copper (II) benzoate, hydrates thereof, mixtures of these, and the like.

Above all, preferable is copper(I) iodide (CuI).

The salt of Pd(I) includes dibromo-dipalladium(I), a hydrate thereof, and the like.

The salt of Pd(II) includes palladium(II) acetate, palladium (II) propionate, palladium(II) butanoate, palladium(II) 2-methylpropanoate, palladium(II) 3-methylbutanoate, palladium (II) 2-methylbutanoate, palladium(II) 2-ethylbutanoate, palladium(II) pivalate, palladium(II) 3,3-dimethylbutanoate, palladium(II) 2,2,3,3-tetramethylbutanoate, palladium(II)

trifluoroacetate, palladium(II) nitrate, palladium(II) chloride, palladium(II) bromide, palladium(II) iodide, palladium(II) acetylacetonate, palladium (II) perchlorate, palladium(II) citrate, palladium(II) oxalate, palladium(II) cyclohexanebutyrate, palladium(II) benzoate, palladium(II) stearate, palladium(II) sulfamate, palladium(II) carbonate, palladium(II) thiocyanate, palladium(II) trifluoromethanesulfonate, palladium(II) bis(4-diethylaminodithiobenzil)palladium (II), palladium(II) cyanide, palladium(II) fluoride, palladium(II) boride, palladium(II) borate, palladium(II) hypophosphite, palladium(II) ammonium sulfate, palladium(II) hydroxide, cyclopentadienyl palladium(II), hydrates thereof, mixtures of these, and the like. Above all, preferable is palladium(II) acetate ($Pd(OAc)_2$), palladium(II) propionate ($Pd(O(C=O)CH_2CH_3)_2$), palladium(II) 2-methylpropanoate ($Pd(O(C=O)CH(CH_3)_2)_2$, palladium(II) pivalate ($Pd(OPiv)_2$), palladium(II) chloride ($PdCl_2$), palladium(I) bromide ($Pd_2Br_2$), or palladium(II) hydroxide ($Pd(OH)_2$); especially preferable is palladium(II) acetate ($Pd(OAc)_2$), palladium(II) propionate ($Pd(O(C=O)CH_2CH_3)_2$), palladium(II) 2-methylpropanoate ($Pd(O(C=O)CH(CH_3)_2)_2$, or palladium pivalate ($Pd(OPiv)_2$).

The salt of cobalt(II) includes cobalt(II) acetate, cobalt(II) nitrate, cobalt(II) chloride, cobalt(II) bromide, cobalt(II) iodide, cobalt(II) acetylacetonate, cobalt(II) perchlorate, cobalt(II) citrate, cobalt(II) oxalate, cobalt(II) fumarate, cobalt(II) gluconate, cobalt(II) benzoate, cobalt(II) lactate, cobalt(II) stearate, cobalt(II) sulfamate, cobalt(II) carbonate, cobalt(II) thiocyanate, cobalt(II) fluoride, cobalt(II) phosphate, cobalt(II) sulfate, cobalt(II) hydroxide, cobalt(II) sulfide, hydrates thereof, mixtures of these, and the like. Above all, preferable is cobalt(II) acetate ($Co(OAc)_2$).

The salt of cobalt(III) includes cobalt(III) fluoride, cobalt (III) chloride, cobalt(III) bromide, cobalt(III) iodide, cobalt (III) acetylacetonate, cobalt(III) sulfate, cobalt(III) nitrate, cobalt(III) phosphate, cobalt(III) perchlorate, cobalt(III) cirate, hydrates thereof, mixtures of these, and the like.

The salt of iron(II) includes iron(II) fluoride, iron(II) chloride, iron(II) bromide, iron(II) iodide, iron(II) sulfate, iron(II) nitrate, iron(II) oxalate, iron(II) fumarate, iron(II) acetate, iron(II) lactate, iron(II) gluconate, iron(II) benzoate, iron(II) stearate, iron(II) acetylacetonate, iron(II) sulfide, hydrates thereof, mixtures of these, and the like.

The salt of iron(III) includes iron(III) fluoride, iron (III) chloride, iron(III) bromide, iron(III) iodide, iron(III) sulfate, iron(III) phosphate, iron(III) perchlorate, hydrates thereof, mixtures of these, and the like.

The salt of rhodium(I) includes rhodium(I) chloride, hydrates thereof, mixtures of these, and the like.

The salt of ruthenium(II) includes ruthenium(II) chloride, hydrates thereof, mixtures of these, and the like.

The salt of iridium(III) includes iridium(III) chloride, iridium(III) bromide, iridium(III) acetate, iridium(III) carbonyl, (acetylacetonato)iridium(III), potassium hexachloroiridate(III), potassium pentachloronitrosyliridate(III), iridium (III) 2,4-pentanedionate, (pentamethylcyclopentadienyl) iridium(III) dichloride dimer, dichloro (pentamethylcyclopentadienyl)iridium(III) dimer, (pentamethylcyclopentadienyl)iridium hydrochloride dimer, hydrates thereof, mixtures of these, and the like.

These transition metal compounds may be used as a mixture.

Among these transition metal compounds, the particularly preferable metal species is palladium.

As these transition metal compounds, there may be used compounds to which ligands were coordinated in advance. As such transition metal compounds having the ligands coordinated, there may be mentioned, for example, the following transition metal compounds. However, the present invention is not limited to these.

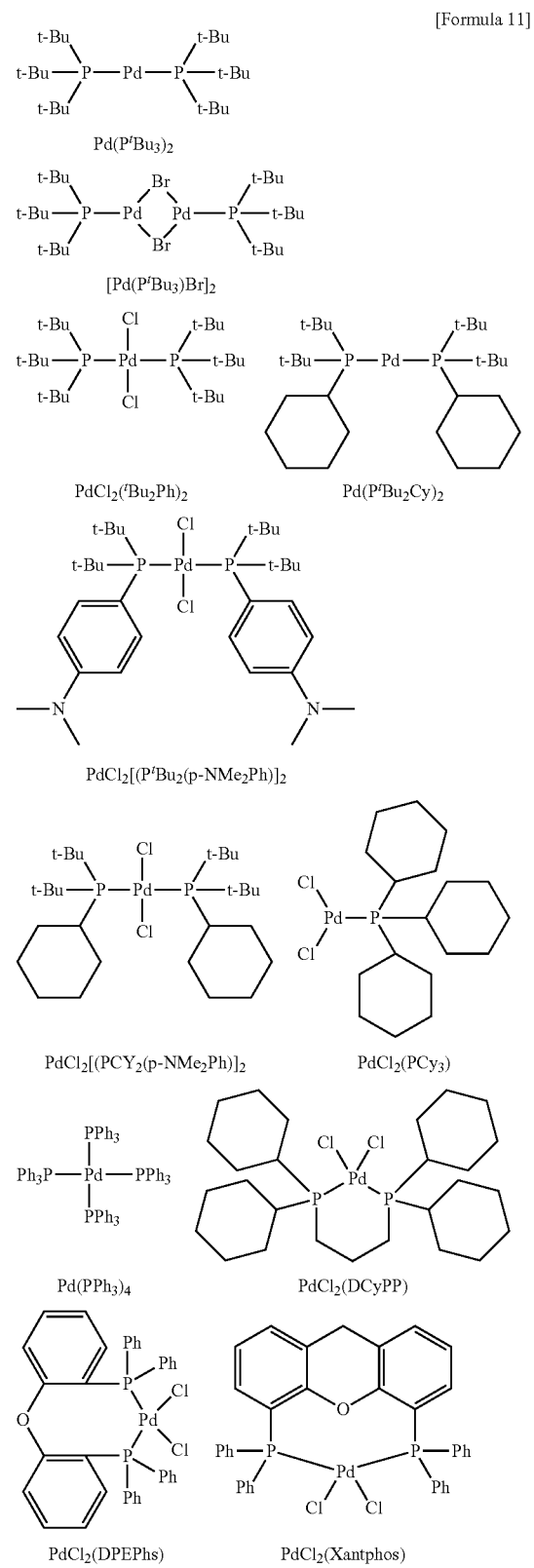

[Formula 11]

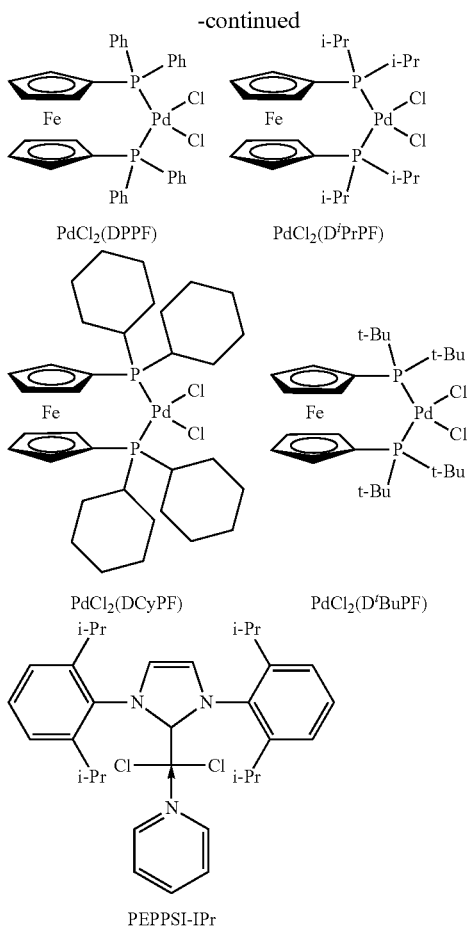

PdCl₂(DPPF)   PdCl₂(D'PrPF)

PdCl₂(DCyPF)   PdCl₂(D'BuPF)

PEPPSI-IPr

In the production process of the present invention, a ligand which can coordinate to the transition metal may be present together with the transition metal compound. The presence of a ligand which can coordinate to the transition metal compound in the reaction facilitate the coupling of the phenyl ring of a phenyl derivative and the C—H bond on the heterocyclic derivative can be coupled with high selectivity, resulting in a higher yield of the compound represented by the formula (3). Such a ligand used in the production process of the present invention includes a carboxylic acid type, amide type, phosphine type, oxime type, sulfide type, sulfonic acid type, 1,3-diketone type, Schiff's base type, oxazoline type, diamine type, hydrocarbon type, carbon monooxide, a carbene type, and the like. However, the present invention is not limited to these. The coordinating atom in the ligand includes a nitrogen atom, phosphorous atom, oxygen atom, sulfur atom, and the like. As the ligand, there are a monodentate ligand having a coordinating atom at one position and a polydentate ligand having coordinating atoms at two or more positions. As for the hydrocarbon type, carbon monoxide, and carbene type, the coordinating atom is the carbon atom. These ligands may be used as salts.

The monodentate ligand includes a phosphine-type ligand represented by $PR^5R^6R^7$ (wherein $R^5$, $R^6$, and $R^7$ each independently represent a $C_1$ to $C_8$ alkyl group, $C_1$ to $C_4$ alkoxy group, $C_3$ to $C_8$ cycloalkyl group, phenyl group, biphenyl group, phenoxy group, and furyl group. The $C_3$ to $C_8$ cycloalkyl group may further be substituted with a $C_1$ to $C_4$ alklyl group. The phenyl group may further be substituted with a methyl group, sulfonic acid group, or a salt thereof. The biphenyl group may further be substituted each independently with a $C_1$ to $C_4$ alklyl group, $C_1$ to $C_4$ alkoxy group, and dimethylamino group), triethylamine, pyridine, and the like.

The phosphine-type ligand represented by $PR^5R^6R^7$ includes, for example, tert-butyldicyclohexylphosphine, isobutyldicyclohexylphosphine, (n-butyl)dicyclohexylphosphine, isopropyldicyclohexylphosphine, (n-propyl)dicyclohexylphosphine, ethyldicyclohexylphosphine, methyldicyclohexylphosphine, cyclopropyldicyclohexylphosphine, cyclobutyldicyclohexylphosphine, tert-butyldicyclooctylphosphine, tert-butyldicycloheptylphosphine, tert-butyldicyclopentylphosphine, tert-butyldicyclobutylphosphine, tert-butyldicyclopropylphosphine, triethylphosphine, tri(n-propyl)phosphine, tri(isopropyl)phosphine, tri(tert-butyl)phosphine, tri(n-butyl)phosphine, tri(n-octyl)phosphine, tri(cyclooctyl)phosphine, tri(cycloheptyl)phosphine, tri(cyclohexyl)phosphine, tri(cyclopentyl)phosphine, tri(cyclobutyl)phosphine, tri(cyclopropyl)phosphine, di(tert-butyl)methylphosphine, di(tert-butyl)ethylphosphine, di(tert-butyl)n-propylphosphine, di(tert-butyl)isopropylphosphine, di(tert-butyl)n-butylphosphine, di(tert-butyl)isobutylphosphine, di(tert-butyl)neopentylphosphine, triphenylphosphine, tri(ortho-tolyl)phosphine, tri(mesityl)phosphine, tri(phenoxy)phosphine, tri(2-furyl)phosphine, trimethoxyphosphine, triethoxyphosphine, tri(n-propyloxy)phosphine, tri(isopropyloxy)phosphine, tri(n-butyloxy)phosphine, tri(isobutyloxy)phosphine, tri(tert-butyloxy)phosphine, di(tert-butyl)cyclohexylphosphine, di(isobutyl)cyclohexylphosphine, di(n-butyl)cyclohexylphosphine, di(isopropyl)cyclohexylphosphine, di(n-propyl)cyclohexylphosphine, diethylcyclohexylphosphine, dimethylcyclohexylphosphine, di(tert-butyl)cyclopentylphosphine, di(isobutyl)cyclopentylphosphine, di(n-butyl)cyclopentylphosphine, di(isopropyl)cyclopentylphosphine, di(n-propyl)cyclopentylphosphine, diethylcyclopentylphosphine, dimethylcyclopentylphosphine, di(tert-butyl)cyclooctylphosphine, di(tert-butyl)cycloheptylphosphine, di(tert-butyl)cyclopentylphosphine, di(tert-butyl)cyclobutylphosphine, di(tert-butyl)cyclopropylphosphine, dimethylphenylphosphine, diethylphenylphosphine, di(n-propyl)phenylphosphine, di(isopropyl)phenylphosphine, di(n-butyl)phenylphosphine, di(isobutyl)phenylphosphine, di(tert-butyl)phenylphosphine, di(cyclooctyl)phenylphosphine, dicycloheptylphenylphosphine, dicyclohexylphenylphosphine, dicyclopentylphenylphosphine, dicyclobutylphenylphosphine, dicyclopropylphenylphosphine, dicyclohexyl(para-tolyl)phosphine, dicyclohexyl(ortho-tolyl)phosphine, dicyclohexyl(para-tolyl)phosphine, dicyclohexyl(2,4,6-trimethylphenyl)phosphine, methyl diphenylphosphine, ethyldiphenylphosphine, (n-propyl)diphenylphosphine, isopropyl diphenylphosphine, (n-butyl)diphenylphosphine, isobutyldiphenylphosphine, (tert-butyl)diphenylphosphine, cyclooctyldiphenylphosphine, cycloheptyldiphenylphosphine, cyclohexyldiphenylphosphine, cyclopentyldiphenylphosphine, cyclobutyldiphenylphosphine, cyclopropyldiphenylphosphine, bis(para-sulfonatophenyl)phenylphosphine potassium, cBRIDP, BippyPhos, TrippyPhos, XPhos (2-dicyclohexylphosphino-2',4',6'-triisopropyl-1,1'-biphenyl), t-Bu-XPhos, JohnPhos, Cy-JohnPhos, MePhos, t-Bu-MePhos, DavePhos, t-Bu-DavePhos, SPhos, RuPhos (2-dicyclohexylphosphino-2',6'-diisopropoxy-1,1'-biphenyl), cataCXium A, cataCXium ABn, cataCXium PtB, cataCXium PCy, cataCXium POMetB, cataCXium POMeCy, cataCXium PIntB, cataCXium PInCy, cataCXium PICy, Q-Phos, JOSIPHOS, and the like; and mixtures of these.

(Formula 12)

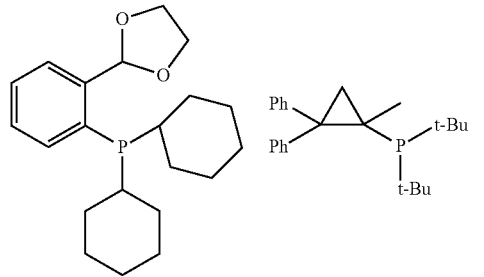

BippyPhos / cBRIDP / TrippyPhos

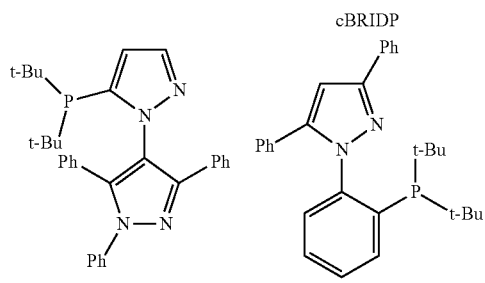

XPhos (R = Cyclohexyl)
t-Bu-XPhos (R = t-Bu)

JohnPhos (R = Cyclohexyl)
Cy-JohnPhos (R = t-Bu)

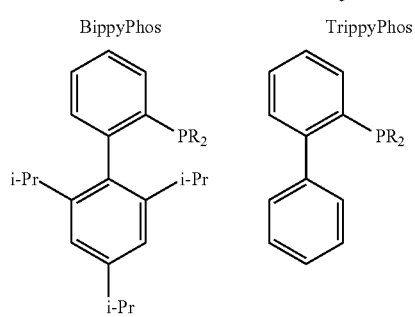

MePhos (R = Cyclohexyl)
t-Bu-MePhos (R = t-Bu)

DavePhos (R = Cyclohexyl)
t-Bu-MePhos (R = t-Bu)

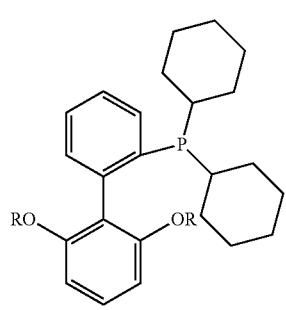

SPhos (R = Methyl)
RuPhos (R = i-Pr)

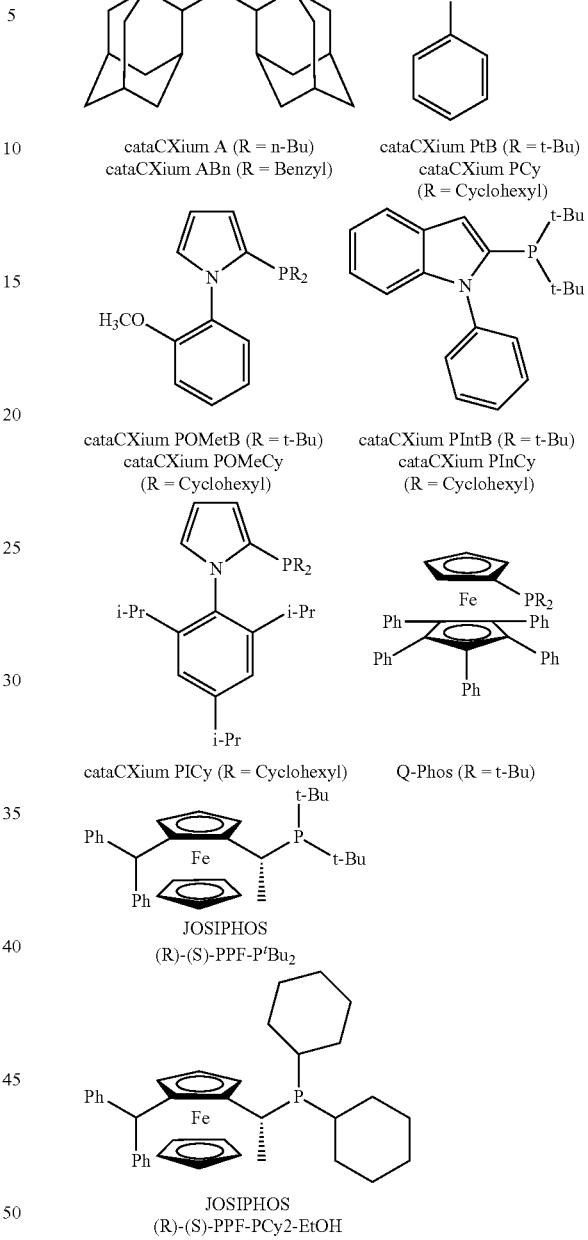

cataCXium A (R = n-Bu)
cataCXium ABn (R = Benzyl)

cataCXium PtB (R = t-Bu)
cataCXium PCy (R = Cyclohexyl)

cataCXium POMetB (R = t-Bu)
cataCXium POMeCy (R = Cyclohexyl)

cataCXium PIntB (R = t-Bu)
cataCXium PInCy (R = Cyclohexyl)

cataCXium PICy (R = Cyclohexyl)   Q-Phos (R = t-Bu)

JOSIPHOS
(R)-(S)-PPF-P^tBu_2

JOSIPHOS
(R)-(S)-PPF-PCy2-EtOH

The bidendate ligand includes 2,2'-bipyridyl, 4,4'-(tert-butyl)bipyridyl, phenanthroline, 2,2'-bipyrimidyl, 1,4-diazabicyclo[2.2.2]octane, 2-(dimethylamino)ethanol, tetramethylethylenediamine, N,N-dimethylethylenediamine, N,N'-dimethylethylenediamine, 2-aminomethylpyridine, (NE)-N-(pyridin-2-ylmethylidene)aniline, 1,1'-bis(diphenylphosphino)ferrocene, 1,1'-bis(tert-butyl)ferrocene, diphenylphosphinomethane, 1,2-bis(diphenylphosphino)ethane, 1,3-bis(diphenylphosphino)propane, 1,5-bis(diphenylphosphino)pentane, 1,2-bis(dipentafluorophenylphosphino)ethane, 1,2-bis(dicyclohexylphosphino) ethane, 1,3-(dicyclohexylphosphino)propane, 1,2-bis(di-tert-butylphosphino)ethane, 1,3-bis(di-tert-butylphosphino)propane, 1,2-bis(diphenylphosphino)benzene, 1,5-cyclooctadiene, BINAP, BIPHEMP, PROPHOS, DIOP, DEGUPHOS, DIPAMP, DuPHOS, NORPHOS, PNNP, SKEWPHOS, BPPFA, SEGPHOS, CHIRAPHOS, DPEphos, Xantphos, and the like; and mixtures of these.

[Formula 13]

DPEphos

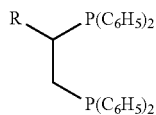
PROPHOS
PROPHOS(R = CH$_3$)
BENZPHOS(R = C$_6$H$_5$CH$_2$)
CyCPHOS(R = C$_6$H$_{11}$)

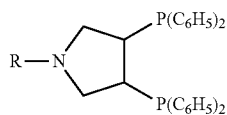
DEGUPHOS

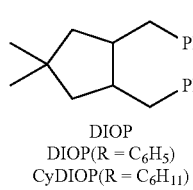
DIOP
DIOP(R = C$_6$H$_5$)
CyDIOP(R = C$_6$H$_{11}$)

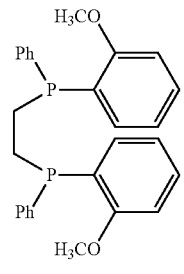
DIPAMP

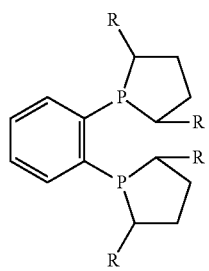
DuPHOS
Me-DuPHOS(R = CH$_3$)
Et-DuPHOS(R = C$_2$H$_5$)
i-Pr-DuPHOS(R = i-Pr)

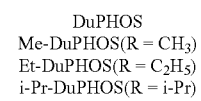
NORPHOS

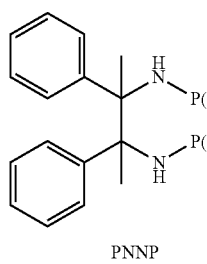
PNNP

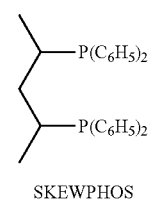
SKEWPHOS

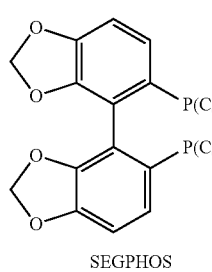
SEGPHOS

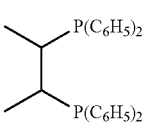
CHIRAPHOS

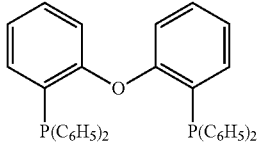
DPEphos

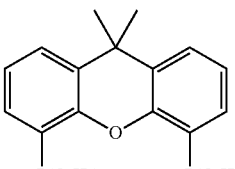
Xantphos

H$_8$-BINAP

BINAP includes derivatives thereof and specific examples include 2,2'-bis(diphenylphosphino)-1,1'-binaphthyl, 2,2'-bis(di-para-tolylphosphino)-1,1'-binaphthyl, 2,2'-bis(di-para-tert-butylphenylphosphino)-1,1'-binaphthyl, 2,2'-bis(di-meta-tolylphosphino)-1,1'-binaphthyl, 2,2'-bis(di-3,5-dimethylphenylphosphino)-1,1'-binaphthyl, 2,2'-bis(di-para-methoxyphenylphosphino)-1,1'-binaphthyl, 2,2'-bis(dicyclopentylphosphino)-1,1'-binaphthyl, 2,2'-bis(dicyclohexylphosphino)-1,1'-binaphthyl, 2-di(β-naphthyl)phosphino-2'-diphenylphosphino-1,1'-binaphthyl, 2-diphenylphosphino-2'-di(para-trifluoromethylphenyl)phosphino-1,1'-binaphthyl, and the like.

BIPHEMP includes derivatives thereof and specific examples include 2,2'-dimethyl-6,6'-bis(diphenylphosphino)-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-para-tolylphosphino)-1,1'-biphenyl, 2,2'-dimethyl-6,6'-bis(di-para-tert-butylphenylphosphino)-1,1'-biphenyl, 2,2',4,4'-tetramethyl-3,3'-dimethoxy-6,6'-bis(di-para-methoxyphenylphosphino)-1,1'-biphenyl, and the like.

The ligand used in the reaction of the present invention may be used as a salt. Such a salt includes, for example, a hydrochloric acid salt, hydrobromic acid salt, tetrafluoroboric acid salt, and the like.

When a palladium catalyst is used, the ligand is preferably a phosphine-type ligand. Above all, the phosphine-type ligand represented by PR$^5$R$^6$R$^7$ is preferable. Specifically, preferable is tri(tert-butyl)phosphine, tri(cyclohexyl)phosphine, tert-butyldicyclohexylphosphine, di(tert-butyl)cyclohexylphosphine, di(tert-butyl)methylphosphine, 2-dicyclohexylphosphino-2',6'-diisopropoxy-1,1'-biphenyl, 2-dicyclohexylphosphino-2',4',6'-triisopropyl-1,1'-biphenyl, or salts thereof; more preferable is tri(tert-butyl)phosphine, di(tert-butyl)cyclohexylphosphine, or a salt thereof; and particularly preferable is di(tert-butyl)cyclohexylphosphine or a salt thereof.

When the ligand is coordinated in advance, a preferred ligand may be used by coordinating the same to palladium.

The ligand may be used as a mixture. Furthermore, the ligand may be used by coordinating the same to a transition metal compound in advance. In addition, the ligand used in the reaction of the present invention may not be used depending on the circumstances.

In the production process of the present invention, a base may be used together with the transition metal compound. By using the base together, the yield of the compound represented by the formula (3) can be improved. Such a base used in the production process of the present invention is not particularly limited but preferable above all is lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate, potassium acetate, and the like; a $C_1$ to $C_6$ alkoxide metal salt (lithium salt, sodium salt, potassium salt, and magnesium salt); $C_1$ to $C_6$ alkyl anion metal salt (lithium salt, sodium salt, potassium salt, and magnesium salt); tetra($C_1$ to $C_4$ alkyl)ammonium salt (fluoride salt, chloride salt, and bromide salt), diisopropylethylamine, tributylamine, N-methylmorpholine, diazabicycloundecene, diazabicyclooctane, imidazole; or the like.

In the "$C_1$ to $C_6$ alkoxide metal salt (lithium salt, sodium salt, potassium salt, and magnesium salt)" used as a base in the production process of the present invention, the "$C_1$ to $C_6$ alkoxide" includes methoxide, ethoxide, n-propoxide, isopropoxide, n-butoxide, isobutoxide, tert-butoxide, n-pentoxide, isopentoxide, neopentoxide, 1-methylpropoxide, n-hexoxide, isohexoxide, 1,1-dimethylbutoxide, 2,2-dimethylbutoxide, 3,3-dimethylbutoxide, and the like. Furthermore, there may be used mixtures of these.

In the "$C_1$ to $C_6$ alkyl anion metal salt (lithium salt, sodium salt, potassium salt, and magnesium salt)" used as a base in the reaction of the present invention, the "$C_1$ to $C_6$ alkyl anion" includes a methyl anion, ethyl anion, n-propyl anion, isopropyl anion, n-butyl anion, isobutyl anion, tert-butyl anion, n-pentyl anion, isopentyl anion, neopentyl anion, 1-methylpropyl anion, n-hexyl anion, isohexyl anion, 1,1-dimethylbutyl anion, 2,2-dimethylbutyl anion, 3,3-dimethylbutyl anion, and the like. Furthermore, there may be used mixtures of these.

When a palladium catalyst is used, the base is preferably potassium carbonate; potassium bicarbonate, cesium carbonate, or tetra(n-butyl)ammonium fluoride; particularly preferably potassium carbonate or cesium carbonate.

When a copper catalyst is used, the preferable base is potassium phosphate. When a cobalt catalyst is used, the preferable base is cesium fluoride.

Depending on the circumstances, the base used in the present reaction may not be used.

In the production process of the present invention, a reducing agent which reduces the transition metal may be used together with the transition metal compound. For example, there may be mentioned zinc and the like.

In the production process of the present invention, there may be added a silver salt. By addition of the silver salt may further improve the yield of the compound represented by the formula (3). Such a silver salt includes, for example, silver carbonate and the like.

In the production process of the present invention, there may be added a $C_1$ to $C_{12}$ carboxylic acid or salt thereof. The addition of the $C_1$ to $C_{12}$ carboxylic acid or salt thereof may further improve the yield of the compound represented by formula (3) and/or the rate of the reaction. These $C_1$ to $C_{12}$ carboxylic acids and salts thereof may be used as a mixture. The $C_1$ to $C_{12}$ carboxylic acid has 1 to 12 carbon atoms including the carbon atom of the carboxyl group and may contain a halogen atom, oxo group, and ether bond. The examples include formic acid, acetic acid, propionic acid, butanoic acid, 2-methylpropanoic acid, pentanoic acid, 3-methylbutanoic acid, 2-methylbutanoic acid, pivalic aid, 3,3-dimethylbutanoic acid, 2-methylpentanoic acid, 2-methylhexanoic acid, 2-methylheptanoic acid, pentanecarboxylic acid, hexanoic acid, 4-methylpentanoic acid, 3,3-dimethylbutanoic acid, 2-ethylbutanoic acid, 2-methylpentanoic acid, 3-methylpentanoic acid, 2,2-dimethylbutanoic acid, 2,3-dimethylbutanoic acid, heptanoic acid, 2-methylhexanoic acid, 3-methylhexanoic acid, 4-methylhexanoic acid, 5-methylhexanoic acid, 2,2-dimethylpentanoic acid, 2,3,3-trimethylbutanoic acid, octanoic acid, 2-propylpentanoic acid, 2-ethylhexanoic acid, 2-methylheptanoic acid, 3-methylheptanoic acid, 4-methylheptanoic acid, 6-methylheptanoic acid, 2,2-dimethylheptanoic acid, 3-methylheptanoic acid, 2,2-diethylbutanoic acid, 2,2,4-trimethylpentanoic acid, 2-methyloctanoic acid, 2-methylundecanoic acid, 2-methylnonanoic acid, α-methylcinnamyl acid, cyclopropylacetic acid, 3-cyclopropylpropionic acid, cyclobutylacetic acid, cyclopentylacetic acid, cyclohexylacetic acid, cyclopentylpropionic acid, (2-methylcyclopentyl)acetic acid, cyclopentanecarboxylic acid, 3-oxocyclopentanecarboxylic acid, cyclopropanecarboxylic acid, cyclobutanecarboxylic acid, cyclohexanecarboxylic acid, cycloheptanecarboxylic acid, 1-methylcyclopropanecarboxylic acid, 2-methylcyclopropanecarboxylic acid, 2,2-dimethylcyclopropanecarboxylic acid, 2,2,3,3-tetramethylcyclopropanecarboxylic acid, 2-octylcyclopropanecarboxylic acid, 1-(4-methylphenyl)-1-cyclopropanecarboxylic acid, 2-para-tolylcyclopropanecarboxylic acid, 1-(2-fluorophenyl)cyclopropanecarboxylic acid, 1-(3-fluorophenyl)cyclopropanecarboxylic acid, 1-(4-fluorophenyl)cyclopropanecarboxylic acid, 1-(4-chlorophenyl)cyclopropanecarboxylic acid, 1-(3-chlorophenyl)cyclopropanecarboxylic acid, 2-(4-chlorophenyl)cyclopropanecarboxylic acid, 1-(2,4-dicholorophenyl)cyclopropanecarboxylic acid, 1-(3,4-dichlorophenyl)cyclopropanecarboxylic acid, 2-fluoro-2-phenylcyclopropanecarboxylic acid, 1-(4-methoxyphenyl)cyclopropanecarboxylic acid, 2-(4-(tert-butyl)phenyl)cyclopropanecarboxylic acid, 2,2-difluorocyclopropanecarboxylic acid, 2,2-dichlorocyclopropanecarboxylic acid, 2-chloro-2-fluorocyclopropanecarboxylic acid, 1-trifluoromethylcyclopropanecarboxylic acid, 2,2-dichloro-1-methylcyclopropanecarboxylic acid, cyclopropane-1,1-dicarboxylic acid, 2,2'-oxydiacetic acid, 1,2-dimethylcyclopropanedicarboxylic acid, 4-methylcyclobutanecarboxylic acid, 4-ethylcyclopropanecarboxylic acid, 3-methoxycyclobutanecarboxylic acid, 3-chlorocyclobutanecarboxylic acid, 4-chlorobutanecarboxylic acid, 3-oxo-cyclobutanecarboxylic acid, 3,3-dimethylcyclobutanecarboxylic acid, 1-methylcyclopentanecarboxylic acid, 3-cyclopentenecarboxylic acid, 1-methylcyclopentanecarboxylic acid, 1-methylcyclohexanecarboxylic acid, 4-methylcyclohexanecarboxylic acid, 2-methylcyclohexanecarboxylic acid, 3-methylcyclohexanecarboxylic acid, cyclooctanecarboxylic acid, spiro[2.2]pentane-1-carboxylic acid, Spiro[2.3]hexane-1-carboxylic acid, bicyclo[4.1.0]heptane-7-carboxylic acid, tricyclo[3.2.1.0*2,4*]octane-3-carboxylic acid, bicyclo[6.1.0]nonane-9-carboxylic acid, bicyclo[2.2.1]heptane-1-carboxylic acid, bicyclo[2.2.1]heptane-2-carboxylic acid, 7,7-dimethyltricyclo[2.2.1.0(2,6)]heptane-1-carboxylic acid, 5-norbornene-2-carboxylic acid, norbornane-2-carboxylic acid, 1-adamantanecarboxylic acid, 3-methyladamantane-1-carboxylic acid, 3-fluoroadamantane-1-carboxylic acid, 3,5-dimethyladamantane-1-carboxylic acid, 3-ethyladamantane-1-carboxylic acid, 3-chloroadamantane-1-carboxylic acid, 3,5,7-trimethyladamantane-1-carboxylic acid, 3-bromoadamantane-1-carboxylic acid, 5-bromo-3-methyladamantane-1-carboxylic acid, 5-bromo-3-ethyladamantane-1-carboxylic acid, tetrahydrofuran-2-carboxylic acid, tetrahydrofuran-3-carboxylic acid, tetrahydropyran-4-carboxylic acid, tetrahydropyran-3-carboxylic acid, methoxyacetic acid, trichloroacetic acid, dichloroacetic acid, chloroacetic acid, fluoroacetic acid, 2-fluoro-2-methylpropanoic acid, difluoroacetic acid, 2-chloropropanoic acid, 3-fluoropropionic acid, 2-fluoropropionic acid, 2-chloropropionic acid, 3-chloropropionic acid, 2-chlorobutanoic acid, 3-chlorobutanoic acid, 4-chlorobutanoic acid, 2-chloro-2-methylpropanoic acid, 3-chloro-2,2-dimethylpropanoic acid, 5-chloropentanoic acid, 2-chloro-3-methylbutanoic acid, dichloroacetic acid, 1-fluoro-1-chloroacetic acid, 2,2-difluoropropionic acid, 2,2-difluorobutanoic acid, 2,2-dichloropropionic acid, 2,3-dichloropropionic acid, chlorodifluoroacetic acid, trifluoroacetic acid, 3,3,3-trifluoropropionic acid, 2-methyl-4,4,4-trifluorobutanoic acid, 4,4,4-trifluorobutanoic acid, 2,2,3,3-tetrafluoropropionic acid, 2,3,3,3-tetrafluoropropionic acid, and the like. However, the present invention is not limited to these.

As the $C_1$ to $C_{12}$ carboxylic acid, preferable is a carboxylic acid wherein the carbon atom at the α-position of the carboxyl group is not a carbon atom on an aromatic ring, more preferable being a carboxylic acid which may contain a halogen atom or ether bond. Examples include acetic acid, propionic acid, 2-methylpropanoic acid, 2-ethylbutanoic acid, pivalic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, 2,2'-oxydiacetic acid, cyclopropane-1,1-dicarboxylic acid, and the like.

Above all, preferable is a carboxylic acid having one carboxyl group. Examples include acetic acid, propionic acid, 2-methylpropanoic acid, 2-ethylbutanoic acid, pivalic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, and the like.

Further, more preferable is a carboxylic acid wherein the number of hydrogen atoms bonded to the carbon atom at the α-position of the carboxyl group is 0 or 1. Examples include 2-methylpropanoic acid, 2-ethylbutanoic acid, pivalic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, and the like.

Particularly, more preferable is a carboxylic acid consisting of only carbon atoms and hydrogen atoms except the carboxyl group. Examples include 2-methylpropanoic acid, 2-ethylbutanoic acid, pivalic acid, cyclopropanoic acid, 2,2,3,3-tetramethylcyclopropanoic acid, cyclopentanoic acid, 1-adamantanecarboxylic acid, and the like.

More particularly, preferable is a carboxylic acid having 1 to 8 carbon atoms, more preferable being a carboxylic acid having 1 to 6 carbon atoms. Examples include 2-methylpropanoic acid, 2-ethylbutanoic acid, pivalic acid, cyclopropanoic acid, cyclopentanoic acid, and the like. Even more particularly, preferable is 2-methylpropanoic acid or pivalic acid.

The $C_1$ to $C_{12}$ carboxylic acid used in the reaction of the present invention may be used as a salt. Such a salt includes, for example, alkali metal salts such as a sodium salt, potassium salt, lithium salt, and the like; alkaline earth metal salts such as a calcium salt, magnesium salt, and the like; metal salts such as an aluminum salt, iron salt, and the like; inorganic salts such as an ammonium salt and the like; organic salts such as amine salts including a t-octylamine salt, dibenzylamine salt, morpholine salt, glucosamine salt, phenylglycyl alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenylamine salt, piperazine salt, tetramethylammonium salt, tris(hydroxymethyl)aminomethane salt, and the like.

The $C_1$ to $C_{12}$ carboxylic acid and salt thereof used in the reaction of the present invention can usually be used as an additive. However, if they are commercially available as or easy to prepare as carboxylic acid salts of transition metal compounds (for example, palladium(II) propionate), the transition metal carboxylates may be used.

The production process of the present invention may be carried out in a wide range of temperature. The range is generally 0° C. to 200° C., preferably 0° C. to 150° C. Furthermore, the reaction is preferably carried out under ordinary pressure but may also be carried out under increased pressure or reduced pressure. The reaction time is 0.1 to 72 hours, preferably 0.1 to 48 hours. The reaction can be carried out in air but it is desirable that the reaction is carried out under a gas atmosphere having no ill effect on the reaction, such as argon gas, nitrogen gas, and the like. Furthermore, in the present reaction, microwave may be irradiated.

The solvent used in the production process of the present invention includes aliphatic hydrocarbons (hexane, cyclohexane, heptane, and the like), aliphatic halogenated hydrocarbons (dichloromethane, chloroform, carbon tetrachloride, dichloroethane, and the like), aromatic hydrocarbons (benzene, toluene, mesitylene, chlorobenzene, and the like), ethers (diethyl ether, dibutyl ether, dimethoxyethane (DME), cyclopentyl methyl ether (CPME), tert-butyl methyl ether, tetrahydrofuran, dioxane, and the like), esters (ethyl acetate, ethyl propionate, and the like), acid amides (dimethylforamide (DMF), dimethylacetamide (DMA), N-methylpyrrolidone (NMP), and the like), nitriles (acetonitrile, propionitrile, and the like), dimethyl sulfoxide (DMSO), mixed solvents thereof, and the like.

In the production process of the present invention, the amount used of the compound of the formula (2) may be in a range from 1 mol % to 1000 mol % relative to the compound of the formula (1). The range is preferably 50 mol % to 200 mol %, more preferably 80 mol % to 120 mol %.

In the production process of the present invention, the amount used of the transition metal compound and ligand may be in a range of 100 mol % or less relative to the compound of the formula (1) or the compound of the formula (2). Preferably, the amount is in a range of 20 mol % or less. The ligand may not be used depending on the circumstances.

In the production process of the present invention, the amount used of the base may be in a range of 1000 mol % or less relative to the compound of the formula (1) or the compound of the formula (2). Preferably, the amount is in a range of 500 mol % or less.

In the production process of the present invention, the amount used of the solvent may be 1000 times or less the weight of the compound of the formula (1) or the compound of the formula (2). The amount is preferably 100 times or less, more preferably 20 times or less.

The addition order of the compound of the formula (1), compound of the formula (2), transition metal compound, ligand, base, $C_1$ to $C_{12}$ carboxylic acid, and solvent, which are used in the production process of the present invention, is optional. The best order may be selected depending on the combination of the reagents used.

In the production process of the present invention, the amount used of the $C_1$ to $C_{12}$ carboxylic acid may be 50000 mol % or less relative to the transition metal compound used.

The amount is preferably 5000 mol % or less, more preferably 1000 mol % or less, particularly preferably 500 mol % or less.

In the production process of the present invention, the amount used of the silver salt is 500 mol % or less relative to the compound of the formula (1). Preferably, the amount is 200 mol % or less.

The "mol %" represents a concentration of a certain material, obtained by dividing the number of moles of the certain material by 100 mol of a related material.

The compound represented by the formula (1), which is used in the production process of the present invention, can be produced by the following methods.

Synthetic Method (1):

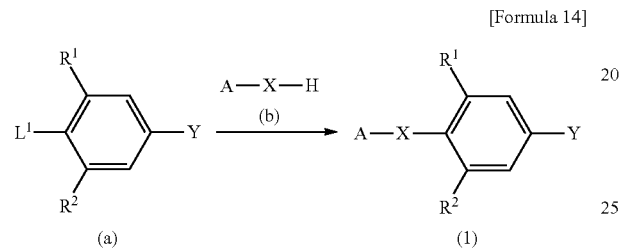

[Formula 14]

(a)     (1)

In the reaction equation, X represents an oxygen atom; $R^1$, $R^2$, A, and Y are the same as defined in the formula (1); $L^1$ represents a leaving group and includes a halogen atom, methanesulfonyloxy group, trifluoromethanesulfonyloxy group, para-toluenesulfonyloxy group, and the like.

Specifically, the compound represented by the formula (1) can be produced by reacting the compound (a) with the compound (b) in the presence of a suitable base in a suitable solvent under a suitable temperature condition.

The solvent used is not particularly limited and includes, for example, aliphatic hydrocarbons (hexane, cyclohexane, heptane, and the like), aliphatic halogenated hydrocarbons (dichloromethane, chloroform, carbon tetrachloride, dichloroethane, and the like), aromatic hydrocarbons (benzene, toluene, xylene, chlorobenzene, mesitylene, and the like), ethers (diethyl ether, dibutyl ether, dimethoxyethane (DME), cyclopentyl methyl ether (CPME), tetrahydrofuran, dioxane, and the like), esters (ethyl acetate, ethyl propionate, and the like), acid amides (dimethylforamide (DMF), dimethylacetamide (DMA), N-methylpyrrolidone (NMP), and the like), nitriles (acetonitrile, propionitrile, and the like), dimethyl sulfoxide (DMSO), water, mixed solvents thereof, and the like.

The base used includes, for example, lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate, potassium acetate, and the like; a $C_1$ to $C_6$ alkoxide metal salt (lithium salt, sodium salt, and potassium salt); $C_1$ to $C_6$ alkyl anion metal salt (lithium salt, sodium salt, and potassium salt); diisopropylethylamine, tributylamine, N-methylmorpholine, diazabicycloundecene, diazabicyclooctane, imidazole; and the like.

For example, the synthesis can be carried out by referring to the Reference Example of the present invention or "Bioorg. Med. Chem. Lett., 2004:14, pp. 2547-2550," etc.

Synthetic Method (2):

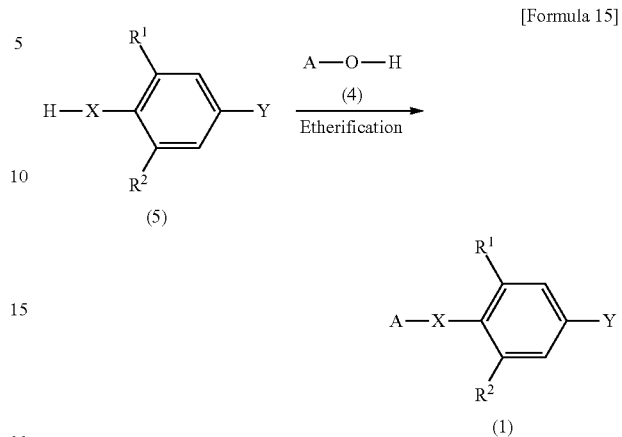

[Formula 15]

(5)

(1)

In the reaction equation, X represents an oxygen atom; $R^1$, $R^2$, A, and Y are the same as defined in the formula (1). This reaction can be carried out by using the Mitsunobu reaction. For example, in the presence of diethyl azodicarboxylate (DEAD), diisopropyl azodicarboxylate (DIAD), 1,1'-(azodicarbonyl)dipiperidine (ADDP), 1,1'-azobis(N,N-dimethylformamide) (TMAD), or the like and in the presence of triphenylphosphine, tributylphosphine, or the like, the reaction can be carried out in a solvent such as tetrahydrofuran, diethyl ether, 1,2-dimethoxyethane, dichloromethane, toluene, or the like at a temperature range of from 0° C. to 150° C.

The compound represented by the formula (1) can be produced by a reaction using the Mitsunobu reaction and its related reactions described in Bull. Chem. Soc. Jpn., 1967:40, p. 2380; Synthesis, 1981, p. 1; and Org. React., 1992:42, p. 335.

Besides the above, the compound represented by the formula (1) can also be synthesized by using an existing general ether synthesis method. For example, the synthesis can be carried out by referring to general text books on synthetic organic chemistry such as Jikken Kagaku Koza 4th ed., No. 20, "Organic Synthesis II Alcohol/Amine," Ed. Chemical Society of Japan (Maruzen Co., Ltd.), pp. 187-205, and the like.

Among the compounds represented by the formula (2), those having a thiazole ring as B are commercially available in some cases but they can be synthesized by referring, for example, to the following scheme:

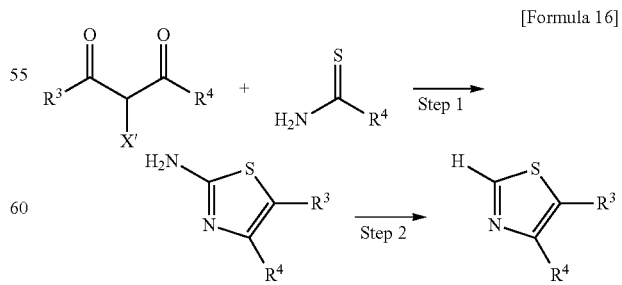

[Formula 16]

The 2-aminothiazole derivative according to the thiazole cyclization reaction of Step 1 can be synthesized by referring to Pharmaceutical Chemistry Journal, 2007:41, pp. 105-108;

Pharmaceutical Chemistry Journal, 2001:35, pp. 96-98; WO 2005/075435; WO 2005/026137; and the like. The reaction of Step 2 can be carried out by reference to Journal of Heterocyclic Chemistry, 1985:22, pp. 1621-1630; Journal of the Chemical Society, Perkin Transactions 1: Organic and Bio-Organic Chemistry, 1982:1, pp. 159-164; and Bioorganic & Medicinal Chemistry Letters, 2008:18, pp. 6231-6235. In addition, the thiazole derivative represented by the formula (2) can be synthesized by referring to, for example, WO 2002/051849 and WO 2001/062250.

Among the compounds represented by the formula (2), various compounds having a pyridine ring as B are commercially available. As well as being purchasable, synthetic methods of these compounds are widely reported and, thus, they can be synthesized by using those techniques.

Among the compounds represented by the formula (2), those having an isoxazole ring or isothiazole ring [in the formula (2), W is an oxygen atom or sulfur atom] are commercially available in some cases. However, they can be synthesized by referring, for example, to the methods described in Tetrahedron Letters, 1968, pp. 5209-5213; Synthesis, 1970, pp. 344-350; Angewandte Chemie, 1967:79, pp. 471-472; and Chemische Berichte, 1973:106, pp. 3291-3311.

EXAMPLES

In the following, the present invention will be described specifically with reference to Examples, etc. However, it should be understood that the scope of the present invention is not limited in any sense by these Examples.

In the present Examples, the analysis and purification were carried out by using the following instruments and the like:
TLC: E. Merck silica gel 60 $F_{254}$ (0.25 mm)
Flash column chromatography: Biotage Flash, Si40
Preparative thin-layer chromatography (PTLC): Merck silica gel 60 $F_{254}$ (1 mm)
Liquid Chromatography/Mass Spectrometry (LC/MS):
  Analytical System: SHIMAZU LCMS-2010A
  Software: LCMS Solution
  Experimental Conditions:
  Column: Phenomenex Gemini 3 μm 4.6 mm×30 mm
  Flow Rate: 1.2 mL/min
  Measurement Temperature: 40° C.
  A-Solvent: 5% MeCN/95% $H_2O$+0.05% TFA
  B-Solvent: 95% MeCN/5% $H_2O$+0.05% TFA
  MS-mode: ESI+
  ESI Voltage: 4.5 KV
  Source Temp: 130° C.
  Desolvation Temp: 320° C.

TABLE 8

| | Time [min] | A [%] | B [%] | Flow [ml/min] |
|---|---|---|---|---|
| 1 | 0.01 | 95 | 5 | 1.2 |
| 2 | 0.3 | 60 | 40 | 1.2 |
| 3 | 2.3 | 0 | 100 | 1.2 |
| 4 | 3.8 | 0 | 100 | 1.2 |
| 5 | 4.0 | 95 | 5 | 1.2 |
| 6 | 4.5 | 95 | 5 | 0 |

A dual column system was employed.
Nuclear Magnetic Resonance (NMR): JEOL JNM-AL400 ($^1$H 400 MHz)
The $^1$H-NMR shift values are shown in ppm with the shift value of tetramethysilane (δ 0.0 p A dual column system was employed. The following abbreviations:

s=singlet, d=doublet, dd=doublet of doublets, t=triplet, q=quartet, m=multiplet, br=broad signal.

In addition, in the $^1$H-NMR spectra in Reference Examples and Examples, the proton signal of a carboxylic acid may not be able to be confirmed in some cases, depending on the measurement conditions such as the solvent and the like.

Reference Example 1

Synthesis of tert-butyl 4-methylthiazole-5-carboxylate

[Formula 17]

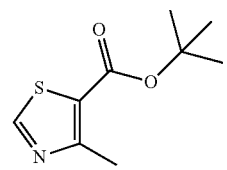

A mixture of 4-methyl-5-thiazolecarboxylic acid (1.36 g, 9.48 mmol) and thionyl chloride (28.7 mL) was stirred at 80° C. for 1 hour. The reaction mixture was concentrated under reduced pressure by removing thionyl chloride and the crude product obtained was dried under reduced pressure. To a solution of this crude material in dichloromethane (5.68 mL), there were added tert-butanol (2.84 mL) and pyridine (16.9 mL) and the mixture was stirred at 60° C. overnight. After the reaction was complete, the reaction mixture was concentrated under reduced pressure. To the crude material obtained were added a saturated aqueous sodium carbonate solution and ethyl acetate. After separating ethyl acetate, extraction was performed by adding ethyl acetate again to the saturated aqueous sodium bicarbonate solution. The combined organic phases were washed with a saturated aqueous sodium chloride solution and dried over anhydrous magnesium sulfate. After removing magnesium sulfate by filtration, the solvent was concentrated under reduced pressure. The crude product obtained was purified by silica gel chromatography (hexane/ethyl acetate=85/15) to obtain the title compound (964 mg). Yield, 51%.

$^1$H-NMR (400 MHz, $CDCl_3$): δ 8.72 (s, 1H), 2.74 (s, 3H), 1.58 (s, 9H).

Reference Example 2

Synthesis of 5-iodo-2-isobutoxybenzonitrile

[Formula 18]

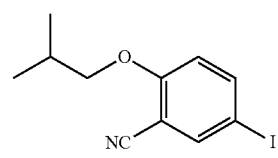

A solution of 2-methyl-1-propanol (0.56 mL, 6.06 mmol) in N,N-dimethylformamide (10 mL) was cooled to 0° C. and to this was added sodium hydride (242 mg, a 60% suspension in mineral oil, 6.06 mmol) in small portions. The turbid reaction mixture was stirred at 0° C. for 5 minutes and the temperature was raised to 23° C. Thereafter, the mixture was stirred at room temperature for 10 minutes and cooled again to 0° C. To the reaction mixture was added 2-fluoro-5-iodobenzonitrile (1.0 g, 4.04 mmol) and, after being warmed to room temperature, the reaction mixture was stirred for 1.5 hours. After the reaction was complete, water (20 mL) was added to the reaction mixture, which was extracted with ethyl acetate (3×30 mL). The organic phases were combined, washed with a saturated aqueous sodium chloride solution (3×30 mL), and thereafter dried over anhydrous magnesium sulfate. After removing magnesium sulfate by filtration, the solvent was concentrated under reduced pressure. The crude product obtained was purified by silica gel chromatography (hexane/ethyl acetate=98/2) to obtain the title compound (950 mg). Yield, 78%.

$^1$H-NMR (400 MHz, CDCl$_3$): δ 7.81 (d, J=2.2 Hz, 1H), 7.76 (dd, J=8.8 Hz, 2.2 Hz, 1H), 6.72 (d, J=8.8 Hz, 1H), 3.80 (d, J=6.3 Hz, 2H), 2.21-2.11 (m, 1H), 1.06 (d, J=6.8 Hz, 6H).

Reference Example 3

Synthesis of 5-bromo-2-isobutoxybenzonitrile

[Formula 19]

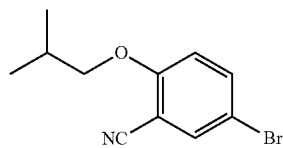

A suspension of sodium hydride (1.64 g, a 60% suspension in mineral oil, 37.5 mmol) in N,N-dimethylformamide (50 mL) was cooled to 0° C. and thereafter 2-methyl-1-propanol (3.47 mL, 37.5 mmol) was added thereto in small portions. The reaction mixture was stirred at room temperature for 20 minutes. The mixture was cooled again to 0° C., 2-fluoro-5-bromobenzonitrile (5.00 g, 25.0 mmol) was added thereto in small portions, and thereafter the reaction mixture was stirred at room temperature for 15 hours. After the reaction was complete, water (100 mL) was added to the reaction mixture, which was then extracted with ethyl acetate (3×100 mL). The organic phases were combined, washed with a saturated aqueous sodium chloride solution (2×50 mL), and thereafter dried over anhydrous sodium sulfate. After removing sodium sulfate by filtration, the solvent was concentrated under reduced pressure. The crude product obtained was purified by silica gel chromatography (hexane/ethyl acetate=9/1) to obtain the title compound (6.04 g). Yield, 95%.

$^1$H-NMR (400 MHz, CDCl$_3$): δ 7.65 (d, J=2.4 Hz, 1H), 7.60 (d, J=9.0 Hz, 2.4 Hz, 1H), 6.84 (d, J=8.8 Hz, 1H), 3.81 (d, J=6.6 Hz, 2H), 2.22-2.12 (m, 1H), 1.06 (d, J=6.6 Hz, 6H).

Example 1

Synthesis of tert-butyl 2-(3-cyano-4-isobutoxyphenyl)-4-methylthiazole-5-carboxylate

[Formula 20]

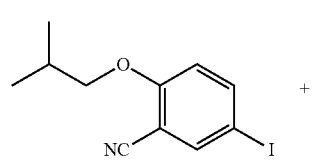 +

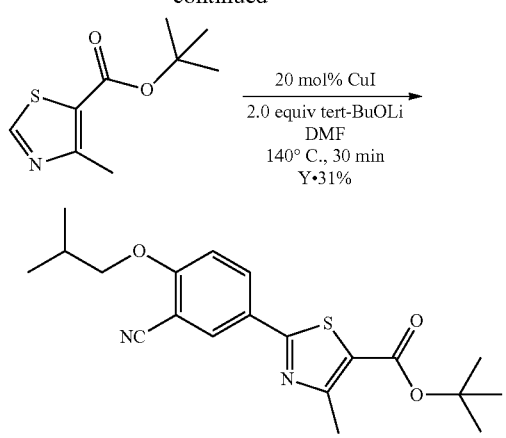

To a reaction vessel were added tert-butyl 4-methylthiazole-5-carboxylate (49.8 mg, 0.25 mmol) obtained in Reference Example 1, 5-iodo-2-isobutoxybenzonitrile (112.9 mg, 0.375 mmol) obtained in Reference Example 2, and anhydrous N,N-dimethylformamide (1.25 mL). After adding tert-butoxy lithium (40.0 mg, 0.5 mmol) and copper(I) iodide (9.5 mg, 0.05 mmol) to the mixture under a nitrogen atmosphere, the reaction mixture was heated to 140° C. and stirred for 30 minutes. After the reaction was complete, the reaction mixture was cooled to room temperature. Water was added to the reaction mixture, which was then extracted with ethyl acetate. The combined organic phases were washed with a saturated aqueous sodium chloride solution and dried over magnesium sulfate. After removing magnesium sulfate by filtration, the organic solvent was concentrated under reduced pressure. The crude product obtained was purified by thin-layer silica gel chromatography (hexane/ethyl acetate=4/1) to obtain the title compound (29.2 mg). Yield, 31%.

$^1$H-NMR (400 MHz, CDCl$_3$): δ 8.16 (d, J=2.4 Hz, 1H), 8.08 (dd, J=8.8 Hz, 2.4 Hz, 1H), 7.00 (d, J=8.8 Hz, 1H), 3.89 (d, J=6.8 Hz, 2H), 2.73 (s, 3H), 2.24-2.16 (m, 1H), 1.59 (s, 9H), 1.09 (d, J=6.8 Hz, 6H).

Example 2

Synthesis of tert-butyl 2-(3-cyano-4-isobutoxyphenyl)-4-methylthiazole-5-carboxylate

[Formula 21]

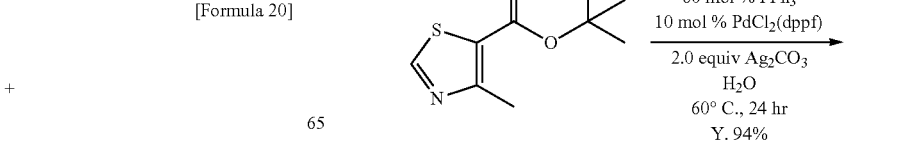 +

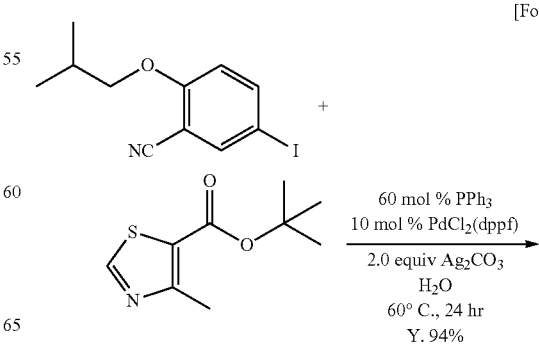

35

-continued

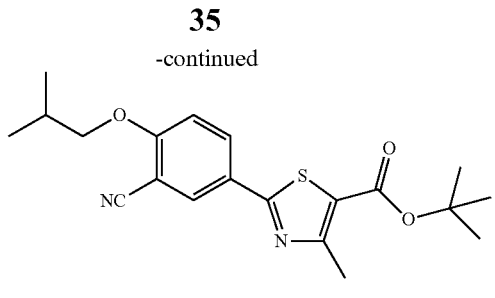

To a reaction vessel were added tert-butyl 4-methylthiazole-5-carboxylate (49.8 mg, 0.25 mmol) obtained in Reference Example 1, 5-iodo-2-isobutoxybenzonitrile (112.9 mg, 0.375 mmol) obtained in Reference Example 2, and water (0.5 mL). Under a nitrogen atmosphere, a complex of palladium (II) chloride with bidentate 1,1'-bis(diphenylphosphino)ferrocene [PdCl$_2$(dppf)] (20.7 mg, 0.025 mmol), triphenylphosphine (39.3 mg, 0.15 mmol), and silver carbonate (138.4 mg, 0.5 mmol) were added and, thereafter, the reaction mixture was heated to 60° C. and stirred for 24 hours. After the reaction was complete, the reaction mixture was cooled to room temperature. Ethyl acetate (2.5 mL) was added to the reaction mixture, and insoluble material was separated by filtration and the filtrate was washed with ethyl acetate. The filtrate was extracted with ethyl acetate twice. The combined organic phases were washed with a saturated aqueous sodium chloride solution and dried over magnesium sulfate. After removing magnesium sulfate by filtration, the organic solvent was concentrated under reduced pressure. The crude product obtained was purified by thin-layer silica gel chromatography (hexane/ethyl acetate=3/1) to obtain the title compound (87.6 mg). Yield, 94%.

$^1$H-NMR (400 MHz, CDCl$_3$): δ 8.16 (d, J=2.4 Hz, 1H), 8.08 (dd, J=8.8 Hz, 2.4 Hz, 1H), 7.00 (d, J=8.8 Hz, 1H), 3.89 (d, J=6.8 Hz, 2H), 2.73 (s, 3H), 2.24-2.16 (m, 1H), 1.59 (s, 9H), 1.09 (d, J=6.8 Hz, 6H).

Example 3

Synthesis of tert-butyl 2-(3-cyano-4-isobutoxyphenyl)-4-methylthiazole-5-carboxylate

[Formula 22]

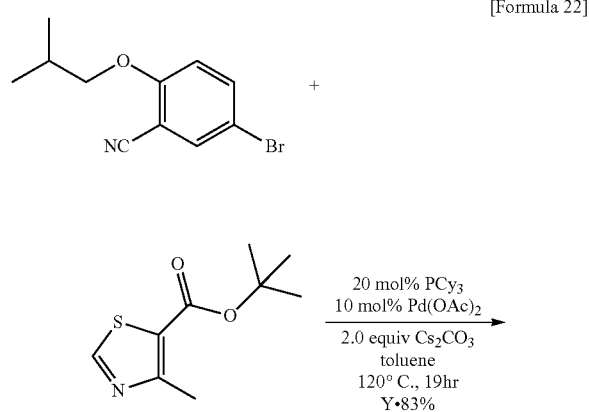

36

-continued

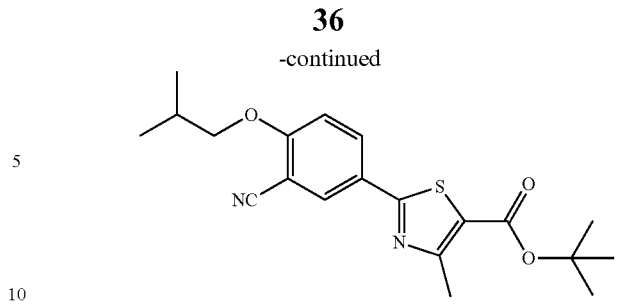

To a test tube-type reaction vessel (50 mL) were added tert-butyl 4-methylthiazole-5-carboxylate (598 mg, 3.0 mmol) obtained in Reference Example 1, 5-bromo-2-isobutoxybenzonitrile (762 mg, 3.0 mmol) obtained in Reference Example 3, palladium acetate (67.4 mg, 0.30 mmol), tri(cyclohexyl)phosphine (168 mg, 0.60 mmol), cesium carbonate (1.95 g, 6.0 mmol), and toluene (11 mL). Thereafter, the reaction vessel was filled with nitrogen, heated to 120° C. under airtight seal, and the reaction mixture was stirred for 19 hours. After the reaction was complete, ethyl acetate (30 mL) was added to the reaction mixture and insoluble matter was removed by filtration. To the filtrate was added 0.1 mol/L hydrochloric acid (20 mL) and the organic phase was extracted and separated. Further, the aqueous phase was extracted with ethyl acetate (20 mL). The combined organic phases were washed with water (30 mL) and a saturated aqueous sodium chloride solution (30 mL) and dried over sodium sulfate. After removing sodium sulfate by filtration, the organic solvent was concentrated under reduced pressure. The crude product obtained was purified by silica gel chromatography (hexane/ethyl acetate=7/1) to obtain the title compound (930 mg). Yield, 83%.

$^1$H-NMR (400 MHz, CDCl$_3$): δ 8.16 (d, J=2.44 Hz, 1H), 8.08 (dd, J=8.78 Hz, 2.20 Hz, 1H), 7.00 (d, J=8.78 Hz, 1H), 3.90 (d, J=6.59 Hz, 2H), 2.73 (s, 3H), 2.25-2.16 (m, 1H), 1.59 (s, 9H), 1.09 (d, J=6.83 Hz, 6H).

Example 4

Synthesis of tert-butyl 2-(3-cyano-4-isobutoxyphenyl)-4-methylthiazole-5-carboxylate

[Formula 23]

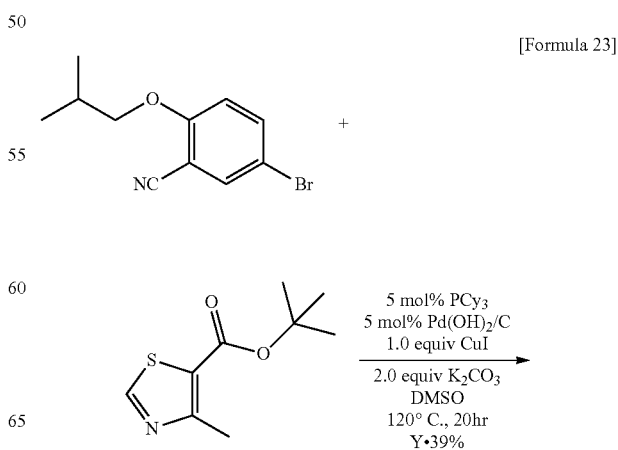

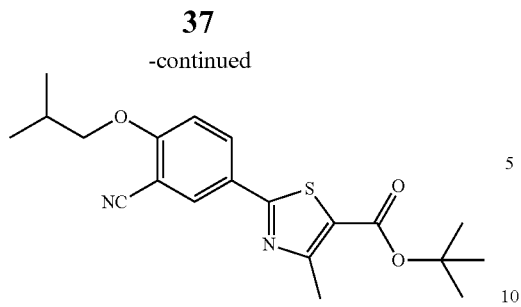

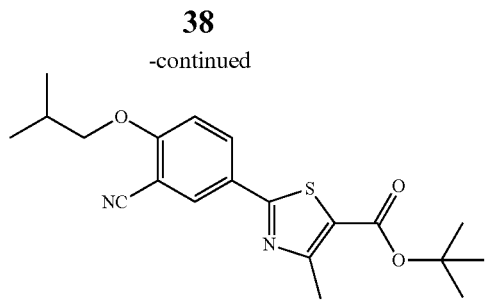

To a test tube-type reaction vessel were added tert-butyl 4-methylthiazole-5-carboxylate (180 mg, 0.903 mmol) obtained in Reference Example 1, 5-bromo-2-isobutoxybenzonitrile (230 mg, 0.903 mmol) obtained in Reference Example 3, palladium hydroxide (31.7 mg, 0.045 mmol), tri(cyclohexyl)phosphine (12.7 mg, 0.045 mmol), potassium carbonate (250 mg, 1.81 mmol), copper iodide (172 mg, 0.903 mmol), and dimethyl sulfoxide (3.0 mL). Thereafter, the reaction vessel was filled with nitrogen, heated to 120° C. under airtight seal, and the reaction mixture was stirred for 20 hours. After the reaction was complete, ethyl acetate (10 mL) and water (10 mL) were added to the reaction mixture, and the resultant mixture was stirred at room temperature for 30 minutes. The solution was filtered through Celite and the Celite layer was washed with ethyl acetate (20 mL) and water (10 mL). The organic phase was separated from the filtrate and the aqueous phase was extracted further with ethyl acetate (20 mL). The combined organic phases were washed with a saturated aqueous sodium chloride solution (10 mL) and dried over sodium sulfate. After removing sodium sulfate by filtration, the organic solvent was concentrated under reduced pressure. The crude product obtained was purified by silica gel chromatography (hexane/ethyl acetate=49/1 to 4/1) to obtain a crude product of the title compound (188 mg). After dissolving this again in ethanol (3 mL) by heating (80° C.), the solution was cooled to 10° C. and the precipitated solid was separated by filtration and washed with ethanol (2 mL). The solid was dried at room temperature under reduced pressure to obtain the title compound (132 mg). Yield, 39%.

$^1$H-NMR (400 MHz, CDCl$_3$): δ 8.17 (d, J=2.20 Hz, 1H), 8.08 (dd, J=8.90 Hz, 2.32 Hz, 1H), 7.00 (d, J=9.02 Hz, 1H), 3.90 (d, J=6.59 Hz, 2H), 2.73 (s, 3H), 2.24-2.15 (m, 1H), 1.59 (s, 9H), 1.09 (d, J=6.83 Hz, 6H).

Example 5

Synthesis of tert-butyl 2-(3-cyano-4-isobutoxyphenyl)-4-methylthiazole-5-carboxylate

[Formula 24]

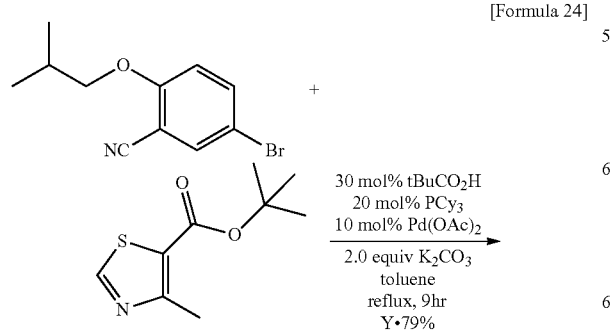

To a reaction vessel were added tert-butyl 4-methylthiazole-5-carboxylate (598 mg, 3.0 mmol) obtained in Reference Example 1, 5-bromo-2-isobutoxybenzonitrile (762 mg, 3.0 mmol) obtained in Reference Example 3, palladium acetate (67.4 mg, 0.30 mmol), tri(cyclohexyl)phosphine (168 mg, 0.60 mmol), potassium carbonate (829 mg, 6.0 mmol), toluene (10 mL), and pivalic acid (92 mg, 0.90 mmol). Thereafter, the reaction mixture was stirred at room temperature for 30 minutes under a nitrogen atmosphere and for further 9 hours with heating under reflux. After the reaction was complete, water (20 mL) and ethyl acetate (20 mL) were added to the reaction mixture and the organic phase was extracted and separated. Further, the aqueous phase was extracted with ethyl acetate (20 mL). The combined organic phases were dried over magnesium sulfate. After removing magnesium sulfate by filtration, the organic solvent was concentrated under reduced pressure. The crude product obtained was purified by silica gel chromatography (hexane/ethyl acetate=100/0 to 0/100) to obtain the title compound (880 mg). Yield, 79%.

$^1$H-NMR (400 MHz, CDCl$_3$): δ 8.16 (d, J=2.20 Hz, 1H), 8.08 (dd, J=8.78 Hz, 2.20 Hz, 1H), 7.00 (d, J=8.78 Hz, 1H), 3.90 (d, J=6.34 Hz, 2H), 2.73 (s, 3H), 2.25-2.15 (m, 1H), 1.59 (s, 9H), 1.09 (d, J=6.59 Hz, 6H).

Example 6

Synthesis of ethyl 2-(3-cyano-4-isobutoxyphenyl)-4-methylthiazole-5-carboxylate

[Formula 25]

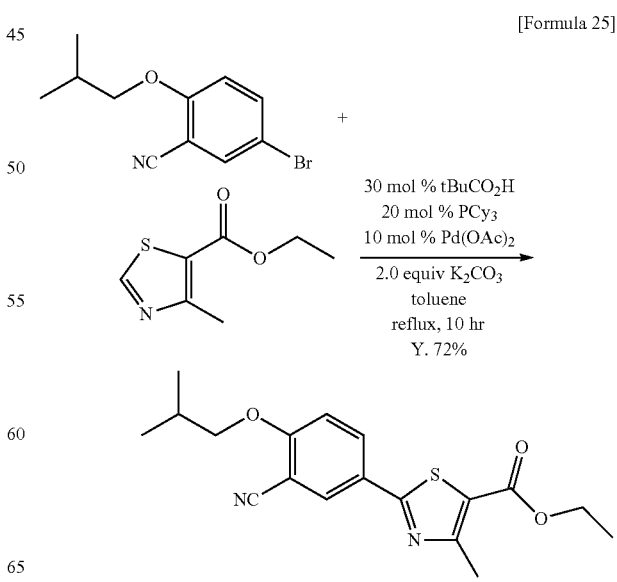

To a reaction vessel were added ethyl 4-methylthiazole-5-carboxylate (514 mg, 3.0 mmol), 5-bromo-2-isobutoxybenzonitrile (762 mg, 3.0 mmol) obtained in Reference Example 3, palladium acetate (67.4 mg, 0.30 mmol), tri(cyclohexyl)phosphine (168 mg, 0.60 mmol), potassium carbonate (829 mg, 6.0 mmol), toluene (10 mL), and pivalic acid (92 mg, 0.90 mmol). Thereafter, the reaction mixture was stirred at room temperature for 30 minutes under a nitrogen atmosphere and for further 10 hours with heating under reflux. After the reaction was complete, water (20 mL) and ethyl acetate (20 mL) were added to the reaction mixture and the organic phase was extracted and separated. Further, the aqueous phase was extracted with ethyl acetate (20 mL). The combined organic phases were dried over magnesium sulfate. After removing magnesium sulfate by filtration, the solvent was concentrated under reduced pressure. The crude product obtained was purified by silica gel chromatography (hexane/ethyl acetate=100/0 to 0/100) to obtain the title compound 734 mg). Yield, 71%.

$^1$H-NMR (400 MHz, CDCl$_3$): δ 8.18 (d, J=2.44 Hz, 1H), 8.09 (dd, J=8.78 Hz, 2.20 Hz, 1H), 7.01 (d, J=8.78 Hz, 1H), 4.36 (q, J=7.07 Hz, 2H), 3.90 (d, J=6.34 Hz, 2H), 2.77 (s, 3H), 2.26-2.16 (m, 1H), 1.39 (t, J=7.19 Hz, 3H), 1.09 (d, J=6.83 Hz, 6H).

Example 7

Synthesis of tert-butyl 2-(3-cyano-4-isobutoxyphenyl)-4-methylthiazole-5-carboxylate

[Formula 26]

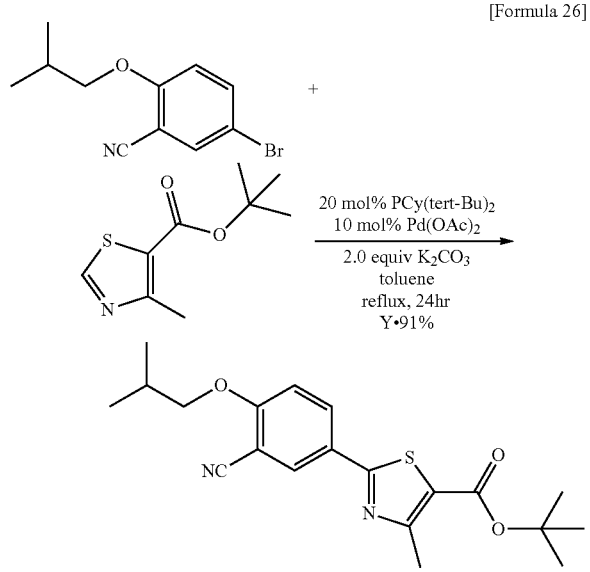

To a reaction vessel were added tert-butyl 4-methylthiazole-5-carboxylate (598 mg, 3.0 mmol) obtained in Reference Example 1, 5-bromo-2-isobutoxybenzonitrile (801 mg, 3.15 mmol) obtained in Reference Example 3, palladium acetate (67.4 mg, 0.30 mmol), di(tert-butyl)cyclohexylphosphine (137 mg, 0.60 mmol), potassium carbonate (829 mg, 6.0 mmol), and toluene (10 mL). Thereafter, the reaction mixture was stirred at room temperature for 30 minutes and for further 24 hours under a nitrogen atmosphere with heating under reflux. After the reaction was complete, water (15 mL) and ethyl acetate (20 mL) were added to the reaction mixture and the organic phase was extracted and separated. Further, the aqueous phase was extracted with ethyl acetate (20 mL). The combined organic phases were dried over magnesium sulfate. After removing magnesium sulfate by filtration, the organic solvent was concentrated under reduced pressure to obtain a crude product. After dissolving the crude product by adding toluene (1 ml) and heating to 70° C., heptane (9 mL) was added thereto at 70° C. and the resultant mixture was allowed to cool to room temperature and further cooled to 0° C. The precipitated solid was separated by filtration, washed with heptane (20 mL) to obtain the title compound (611 mg, 1.64 mmol). Further, the filtrate was concentrated under reduced pressure and the crude product obtained was purified by silica gel chromatography (hexane/ethyl acetate=100/0 to 0/100) to obtain the title compound (405 mg, 1.09 mmol). Yield, 91%.

$^1$H-NMR (400 MHz, CDCl$_3$): δ 8.17 (d, J=2.20 Hz, 1H), 8.09 (dd, J=8.90 Hz, 2.32 Hz, 1H), 7.00 (d, J=8.78 Hz, 1H), 3.90 (d, J=6.34 Hz, 2H), 2.73 (s, 3H), 2.24-2.17 (m, 1H), 1.59 (s, 9H), 1.09 (d, J=6.83 Hz, 6H).

Example 8

Synthesis of ethyl 2-(3-cyano-4-isobutoxyphenyl)-4-methylthiazole-5-carboxylate

[Formula 27]

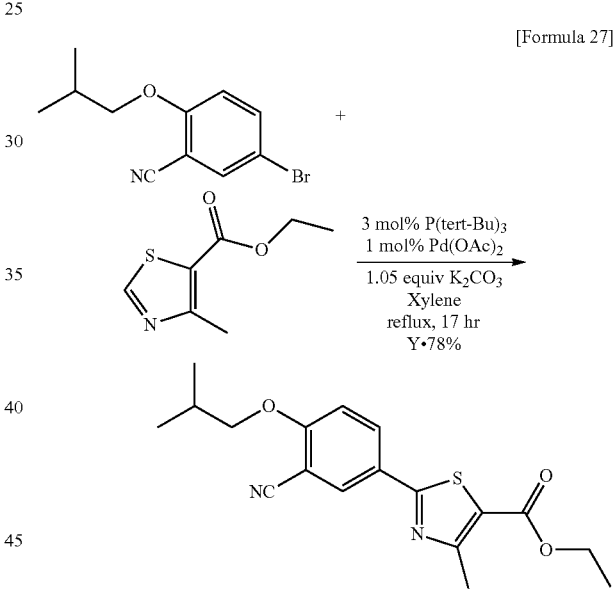

To a reaction vessel were added ethyl 4-methylthiazole-5-carboxylate (1.71 g, 10.0 mmol), 5-bromo-2-isobutoxybenzonitrile (2.54 mg, 10.0 mmol) obtained in Reference Example 3, palladium acetate (22.4 mg, 0.10 mmol), a tetrafluoroboric acid salt of tri(tert-butyl)phosphine (87.0 mg, 0.30 mmol), potassium carbonate (1.45 g, 10.5 mmol), and xylene (10 mL). Thereafter, the reaction mixture was stirred at room temperature for 30 minutes and for further 17 hours under a nitrogen atmosphere, with heating under reflux. After the reaction was complete, the reaction mixture was filtered while hot and the filtration bed was washed with toluene and dichloromethane. The filtrate was concentrated under reduced pressure and the crude product obtained was purified to obtain the title compound (2.69 g). Yield, 78%.

$^1$H-NMR (400 MHz, CDCl$_3$): δ 8.18 (d, J=2.44 Hz, 1H), 8.09 (dd, J=8.78 Hz, 2.20 Hz, 1H), 7.01 (d, J=8.78 Hz, 1H), 4.36 (q, J=7.07 Hz, 2H), 3.90 (d, J=6.34 Hz, 2H), 2.77 (s, 3H), 2.26-2.16 (m, 1H), 1.39 (t, J=7.19 Hz, 3H), 1.09 (d, J=6.83 Hz, 6H).

Example 9

Synthesis of ethyl 2-(3-cyano-4-isobutoxyphenyl)-4-methylthiazole-5-carboxylate

[Formula 28]

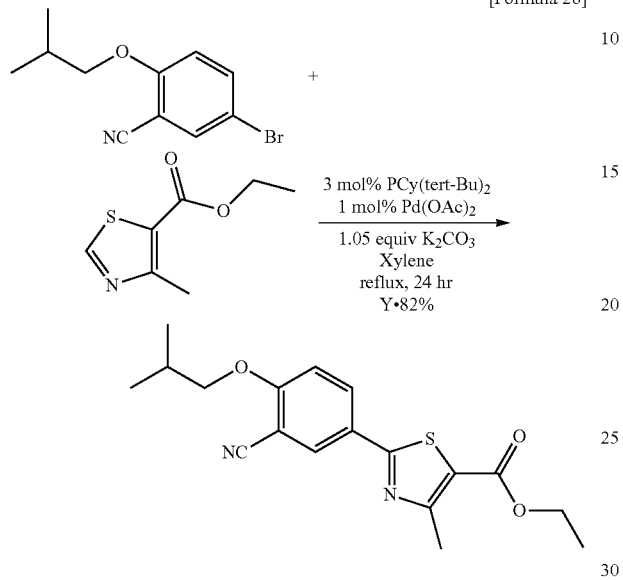

To a reaction vessel were added ethyl 4-methylthiazole-5-carboxylate (1.71 g, 10.0 mmol), 5-bromo-2-isobutoxybenzonitrile (2.69 g, 10.5 mmol) obtained in Reference Example 3, palladium acetate (22.4 mg, 0.10 mmol), di(tert-butyl) cyclohexylphosphine (68.5 mg, 0.30 mmol), potassium carbonate (1.45 g, 10.5 mmol), and xylene (10 mL). Thereafter, the reaction mixture was stirred at room temperature for 30 minutes and for further 24 hours under a nitrogen atmosphere with heating under reflux. After the reaction was complete, the reaction mixture was filtered while hot and the filtration bed was washed with toluene and dichloromethane. The filtrate was concentrated under reduced pressure and the crude product obtained was purified to obtain the title compound (2.83 g). Yield, 82%.

$^1$H-NMR (400 MHz, CDCl$_3$): δ 8.18 (d, J=2.44 Hz, 1H), 8.09 (dd, J=8.78 Hz, 2.20 Hz, 1H), 7.01 (d, J=8.78 Hz, 1H), 4.36 (q, J=7.07 Hz, 2H), 3.90 (d, J=6.34 Hz, 2H), 2.77 (s, 3H), 2.26-2.16 (m, 1H), 1.39 (t, J=7.19 Hz, 3H), 1.09 (d, J=6.83 Hz, 6H).

Example 10

Synthesis of tert-butyl 2-(3-cyano-4-isobutoxyphenyl)-4-methylthiazole-5-carboxylate

[Formula 29]

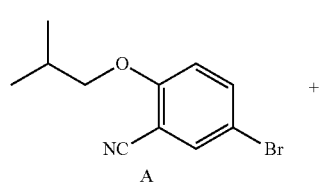

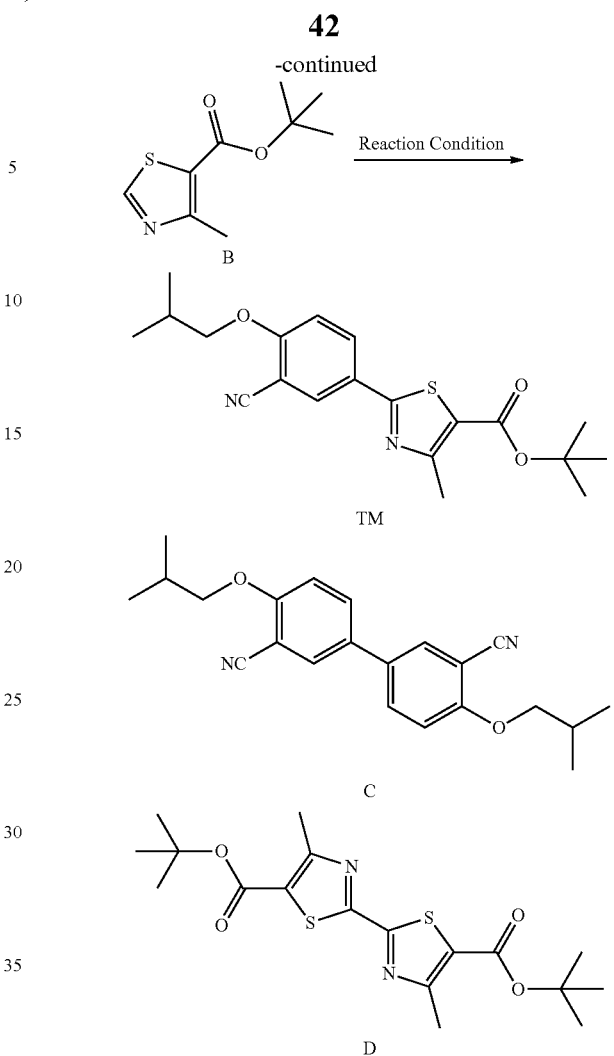

To a test tube-type reaction vessel (10 mL) were added tert-butyl 4-methylthiazole-5-carboxylate (59.8 mg, 0.3 mmol) obtained in Reference Example 1, 5-bromo-2-isobutoxybenzonitrile (76.2 mg, 0.3 mmol) obtained in Reference Example 3, palladium acetate (6.7 mg, 0.030 mmol), a ligand, a base (0.60 mmol), and a solvent (1 mL). Thereafter, the reaction vessel was filled with nitrogen, heated to 120° C. under airtight seal, and the reaction mixture was stirred. After the reaction was complete, a portion of the reaction mixture was diluted with DMSO and the solution obtained was measured by HPLC. The total HPLC area % of the compounds A to D and TM was set as 100% and the calculated yield of the target material was computed from the HPLC area % of the target material. Computation of the calculated yield of the target material from the HPLC area % thereof was carried out by putting the corresponding values in the following calculation formula.

Yield of TM(%)=total amount of TM(mol)/[{total amount of B(mol)+total amount of D(mol)×2+total amount of TM(mol)}/2+{total amount of A(mol)+total amount of (C)×2+total amount of TM(mol)}/2]×100

Total amount of each compound (mol)=HPLC area value (mAU)/HPLC area value per mol of each compound (mAU/mol)

High Performance Liquid Chromatography:
Analytical System: G1315A Hewlett Packard Series 1100
Software: ChemStation for LC 3D
Experimental Conditions:
Column: Imtakt Cadenza CD-C18 4.6×100 mm
Flow: 1.0 mL/min
Wavelength: 254 nm
Temperature: 40° C.
A-Solvent: 5% MeCN/95% $H_2O$+0.05% TFA
B-Solvent: 95% MeCN/5% $H_2O$+0.05% TFA
Gradient:
0-1 min 10% B-Solv.
1-7 min 10-50% B-Solv.
7-14 min 0-80% B-Solv.
14-16 min 80-100% B-Solv.
16-20 min 100% B-Solv.
20-22 min 100-10% B-Solv.
22-25 min 10% B-Solv.

The results in the present Example are shown in the following.

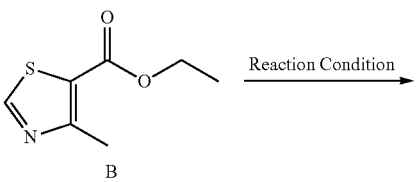

B

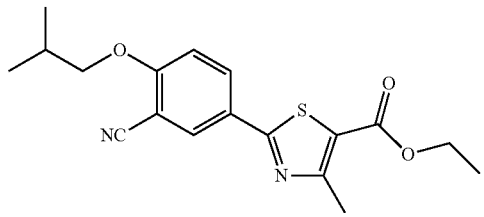

TM

TABLE 9

| Exper-iment No. | Reaction Conditions | | | | | | | HPLC area % | | | | | Cal-culated Yield % |
|---|---|---|---|---|---|---|---|---|---|---|---|---|---|
| | Solvent 0.3M | Base 2 eq. | Pd 0.1 eq. | Ligand 0.2 eq. | Additive 0.3 eq. | Temp-erature °C. | Reaction Time hr | TM | A | B | C | D | TM |
| 1 | DME | $K_2CO_3$ | $Pd(OAc)_2$ | $P(t-Bu)_3 \cdot HBF_4$ (0.4 eq.) | — | 120 | 24 | 63.0 | 4.1 | 21.6 | N.D. | N.D. | 98.8 |
| 2 | NMP | $K_3PO_4$ | $Pd(OAc)_2$ | $P(t-Bu)_3 \cdot HBF_4$ | — | 120 | 24 | 20.8 | 8.2 | 62.1 | 3.7 | N.D. | 89.2 |
| 3 | NMP | $Cs_2CO_3$ | $Pd(OAc)_2$ | $P(t-Bu)_3 \cdot HBF_4$ | — | 120 | 24 | 38.2 | 7.3 | 38.4 | 2.7 | N.D. | 95.0 |
| 4 | Toluene | $Cs_2CO_3$ | $Pd(OAc)_2$ | $PPh_3$ | — | 120 | 24 | 19.5 | 6.4 | 59.6 | 5.6 | N.D. | 65.5 |
| 5 | Toluene | $Cs_2CO_3$ | $Pd(OAc)_2$ | dppp | — | 120 | 24 | 20.8 | 5.7 | 56.9 | 11.6 | N.D. | 65.8 |
| 6 | Toluene | $Cs_2CO_3$ | $Pd(OAc)_2$ | dppe | — | 120 | 24 | 20.5 | 5.4 | 55.5 | 13.5 | N.D. | 64.4 |
| 7 | Toluene | $Cs_2CO_3$ | $Pd(OAc)_2$ | dppf | — | 120 | 24 | 13.5 | 5.8 | 68.8 | 6.4 | N.D. | 61.7 |
| 8 | Toluene | $Cs_2CO_3$ | $Pd(OAc)_2$ | dppb | — | 120 | 24 | 24.9 | 6.0 | 53.7 | 7.8 | N.D. | 71.0 |
| 9 | DME | $Cs_2CO_3$ | $Pd(OAc)_2$ | $PCy_3$ | — | 120 | 19 | 15.3 | 5.9 | 71.6 | 5.2 | N.D. | 90.0 |
| 10 | EA | $K_2CO_3$ | $Pd(OAc)_2$ | $PCy_3$ | PivOH | 120 | 24 | 60.6 | 0.0 | 26.5 | 3.1 | 9.8 | 81.9 |
| 11 | CPME | $K_2CO_3$ | $Pd(OAc)_2$ | $PCy_3$ | PivOH | 120 | 24 | 63.6 | 0.0 | 35.7 | 0.7 | 0.0 | 87.9 |
| 12 | Toluene | $K_2CO_3$ | $Pd(OAc)_2$ | $P(n-Bu)_3$ | PivOH | 120 | 24 | 54.7 | 0.0 | 30.0 | 6.5 | 8.7 | 78.8 |
| 13 | Toluene | $K_2CO_3$ | $Pd(OAc)_2$ | $P(n-Oct.)_3$ | PivOH | 120 | 24 | 55.4 | 0.0 | 28.7 | 7.9 | 8.1 | 79.0 |
| 14 | Toluene | $K_2CO_3$ | $Pd(OAc)_2$ | $PCy_3$ | PivOH | 80 | 90 | 82.7 | 0.0 | 13.1 | 0.0 | 4.2 | 92.9 |

Abbreviations in the Table represent the following:
DME: Dimethoxyethane
NMP: N-Methylpyrrolidone
EA: Ethyl acetate
CPME: Cyclopentyl methyl ether
$HBF_4$: Tetrafluoroboric acid
dppp: 1,1'-Bis(diphenylphosphino)propane
dppe: 1,1'-Bis(diphenylphosphino)ethane
dppb: 1,1'-Bis(diphenylphosphino)butane
dppf: 1,1'-Bis(diphenylphosphino)ferrocene
PCy3: Tricyclohexylphosphine
PivOH: Pivalic acid
n-Oct.: n-Octyl Example 11

Synthesis of ethyl 2-(3-cyano-4-isobutoxyphenyl)-4-methylthiazole-5-carboxylate

[Formula 30]

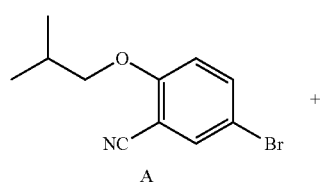

A

+

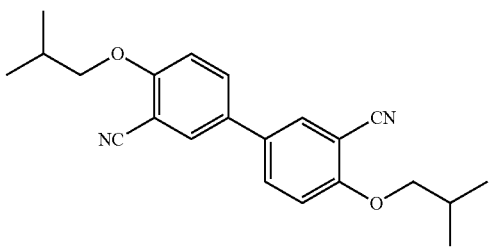

C

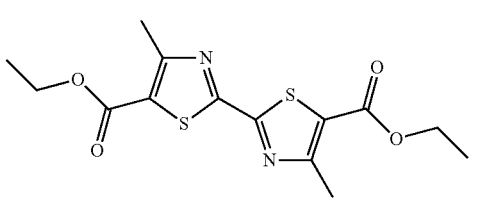

D

To a test tube-type reaction vessel (10 mL) were added ethyl 4-methylthiazole-5-carboxylate (85.5 mg, 0.5 mmol), 5-bromo-2-isobutoxybenzonitrile (127.1 mg, 0.5 mmol) obtained in Reference Example 3, a palladium species, a ligand, a base (1.0 mmol), an additive (0.15 mmol), and a solvent (1.7 mL). Thereafter, the reaction vessel was filled with nitrogen, heated to 120° C. under airtight seal, and the reaction mixture was stirred. After the reaction was complete, a portion of the reaction mixture was diluted with DMSO and the solution obtained was measured by HPLC. The total HPLC area % of the compounds A to D and TM was set as 100% and the calculated yield of the target material was computed from the HPLC area % of the target material. The results are shown in Table 10.

High Performance Liquid Chromatography:
  Analytical System: G1315A Hewlett Packard Series 1100
  Software: ChemStation for LC 3D
  Experimental Conditions:
  Column: Phenomenex Luna Phenyl-Hexyl Sum 4.6×100 mm
  Flow: 1.0 mL/min
  Wavelength: 240 nm
  Temperature: 40° CA-Solvent: 5% MeCN/95% H$_2$O+0.05% TFA
  B-solvent: 95% MeCN/5% H$_2$O+0.05% TFA
  Gradient:
    0-1 min 10% B-Solv.
    1-14 min 10-70% B-Solv.
    14-24 min 70-80% B-Solv.
    24-25 min 80-100% B-Solv.
    25-30 min 100% B-Solv.
    30-32 min 100-10% B-Solv.
    32-35 min 10% B-Solv Abbreviations in the Table represent the following:
AcOH: acetic acid
EtCO$_2$H: propionic acid
i-PrCo$_2$H: 2-methylpropanoic acid Example 12

Synthesis of ethyl 2-(3-cyano-4-isobutoxyphenyl)-4-methylthiazole-5-carboxylate

[Formula 31]

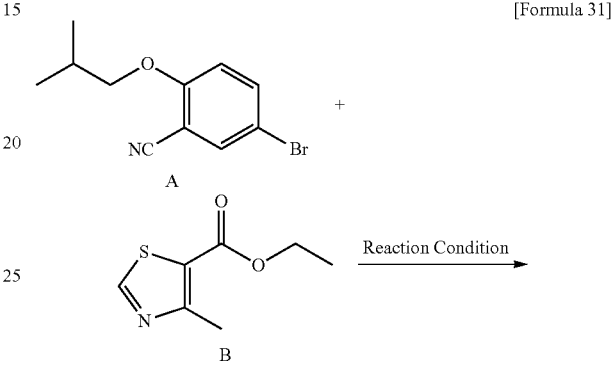

TABLE 10

| Experiment No. | Reaction Conditions | | | | | | | HPLC area % | | | | | Calculated Yield % |
|---|---|---|---|---|---|---|---|---|---|---|---|---|---|
| | Solvent 0.3M | Base 2 eq. | Pd | Ligand | Additive 0.3 eq. | Temperature °C. | Reaction Time hr | TM | A | B | C | D | TM |
| 1 | Toluene | K$_2$CO$_3$ | Pd(OAc)$_2$ (0.1 eq.) | P(t-Bu)$_3$·HBF$_4$ (0.2 eq.) | — | 120 | 5.5 | 31.4 | 39.2 | 29.4 | N.D. | N.D. | 26.5 |
| 2 | Toluene | K$_2$CO$_3$ | Pd(OAc)$_2$ (0.1 eq.) | XPhos (0.2 eq.) | — | 120 | 5.5 | 31.5 | 38.0 | 30.6 | N.D. | N.D. | 26.5 |
| 3 | Toluene | K$_2$CO$_3$ | Pd(OAc)$_2$ (0.1 eq.) | RuPhos (0.2 eq.) | — | 120 | 5.5 | 39.4 | 35.7 | 24.9 | N.D. | N.D. | 34.0 |
| 4 | Toluene | K$_2$CO$_3$ | Pd(OAc)$_2$ (0.02 eq.) | P(t-Bu)$_3$·HBF$_4$ (0.04 eq.) | — | 120 | 15 | 90.1 | 3.3 | 4.1 | 0.7 | 2.1 | 90.7 |
| 5 | Toluene | K$_2$CO$_3$ | Pd(OAc)$_2$ (0.02 eq.) | P(t-Bu)$_3$·HBF$_4$ (0.04 eq.) | — | 120 | 15 | 41.0 | 34.6 | 24.1 | 0.0 | 0.3 | 35.7 |
| 6 | Toluene | K$_2$CO$_3$ | Pd(OAc)$_2$ (0.02 eq.) | P(t-Bu)$_3$·HBF$_4$ (0.04 eq.) | — | 120 | 15 | 46.0 | 30.3 | 22.2 | 0.8 | 0.7 | 40.9 |
| 7 | Toluene | K$_2$CO$_3$ | Pd(OAc)$_2$ (0.02 eq.) | P(t-Bu)$_3$·HBF$_4$ (0.04 eq.) | AcOH | 120 | 15 | 47.5 | 29.6 | 21.9 | 0.6 | 0.4 | 42.1 |
| 8 | Toluene | K$_2$CO$_3$ | Pd(OAc)$_2$ (0.02 eq.) | P(t-Bu)$_3$·HBF$_4$ (0.04 eq.) | PivOH | 120 | 15 | 79.3 | 10.3 | 8.2 | 0.3 | 1.9 | 77.1 |
| 9 | Toluene | K$_2$CO$_3$ | Pd(OAc)$_2$ (0.02 eq.) | P(t-Bu)$_3$·HBF$_4$ (0.04 eq.) | EtCO$_2$H | 120 | 15 | 62.7 | 20.0 | 15.7 | 0.6 | 0.9 | 57.9 |
| 10 | Toluene | K$_2$CO$_3$ | Pd(OAc)$_2$ (0.02 eq.) | P(t-Bu)$_3$·HBF$_4$ (0.04 eq.) | i-PrCO$_2$H | 120 | 15 | 93.4 | 1.0 | 3.9 | 0.6 | 1.2 | 93.7 |
| 11 | Toluene | K$_2$CO$_3$ | Pd(P(t-Bu)$_3$)$_2$ (0.1 eq.) | — | — | 120 | 6 | 8.9 | 50.2 | 40.9 | 0.0 | 0.0 | 7.1 |
| 12 | Toluene | K$_2$CO$_3$ | (Pd(P(t-Bu)$_3$)Br)$_2$ (0.1 eq.) | — | — | 120 | 6 | 11.9 | 49.7 | 36.8 | 1.6 | 0.0 | 9.8 |
| 13 | Toluene | K$_2$CO$_3$ | Pd(P(t-Bu)$_3$)$_2$ (0.1 eq.) | — | PivOH | 120 | 6 | 90.7 | 0.1 | 6.7 | 0.0 | 2.5 | 91.4 |
| 14 | Toluene | K$_2$CO$_3$ | (Pd(P(t-Bu)$_3$)Br)$_2$ (0.1 eq.) | — | PivOH | 120 | 6 | 78.0 | 10.5 | 0.5 | 3.5 | 7.5 | 87.0 |

-continued

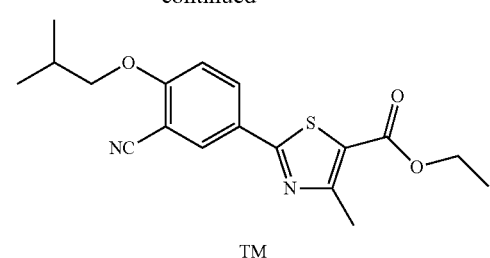
TM

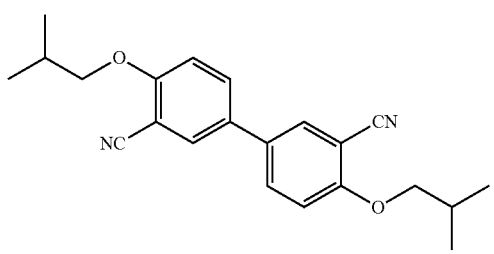
C

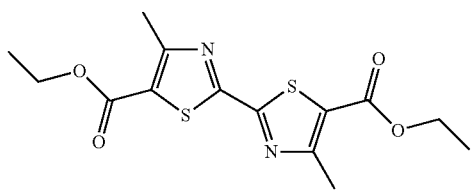
D

To a test tube-type reaction vessel (20 mL) were added ethyl 4-methylthiazole-5-carboxylate (381.2 mg, 1.5 mmol), 5-bromo-2-isobutoxybenzonitrile (256.8 mg, 1.5 mmol) obtained in Reference Example 3, palladium acetate (6.7 mg, 0.030 mmol), di(tert-butyl)cyclohexylphosphine (13.7 mg, 0.060 mmol), potassium carbonate (414.6 mg, 3.0 mmol), an additive (0.45 mmol), and xylene (5.0 mL). Thereafter, the reaction vessel was filled with nitrogen, heated to 120° C. under airtight seal, and the reaction mixture was stirred for 5 hours. After the reaction was complete, a portion of the reaction mixture was diluted with DMSO and the solution obtained was measured by HPLC. The total area % of the compounds A to D and TM was set as 100% and the calculated yield of the target material was computed from the HPLC area % of the target material. The results are shown in Table 11.

High Performance Liquid Chromatography:
Analytical System: G1315A Hewlett Packard Series 1100
Software: ChemStation for LC 3D
Experimental Conditions:
Column: Phenomenex Luna Phenyl-Hexyl 5 urn 4.6×100 mm
Flow: 1.0 mL/min
Wavelength: 240 nm
Temperature: 40° C.
A-Solvent: 5% MeCN/95% $H_2O$+0.05% TFA
B-solvent: 95% MeCN/5% $H_2O$+0.05% TFA
Gradient:
0-1 min 10% B-Solv.
1-14 min 10-70% B-Solv.
14-24 min 70-80% B-Solv.
24-25 min 80-100% B-Solv.
25-30 min 100% B-Solv.
30-32 min 100-10% B-Solv.
32-35 min 10% B-Solv.

TABLE 11

| Experiment No. | Reaction Condition ||||||| HPLC area % ||||| Calculated Yield % |
|---|---|---|---|---|---|---|---|---|---|---|---|---|---|
| | Solvent 0.3M | Base 2 eq. | Pd 0.02 eq. | Ligand 0.04 eq. | Additive 0.3 eq. | Temperature °C. | Reaction Time hr | TM | A | B | C | D | TM |
| 1 | Xylene | — | Pd(OAc)$_2$ | (t-Bu)$_2$PCy | — | 120 | 5 | 1.1 | 59.2 | 39.5 | 0.0 | 0.2 | 0.9 |
| 2 | Xylene | K$_2$CO$_3$ | Pd(OAc)$_2$ | (t-Bu)$_2$PCy | — | 120 | 5 | 31.0 | 40.5 | 27.4 | 0.3 | 0.8 | 26.7 |
| 3 | Xylene | K$_2$CO$_3$ | Pd(OAc)$_2$ | (t-Bu)$_2$PCy | PivOH | 120 | 5 | 74.6 | 13.2 | 9.1 | 0.0 | 3.1 | 72.5 |
| 4 | Xylene | K$_2$CO$_3$ | Pd(OAc)$_2$ | (t-Bu)$_2$PCy | CyPrCO$_2$H | 120 | 5 | 28.7 | 42.5 | 28.7 | 0.0 | 0.1 | 24.3 |
| 5 | Xylene | K$_2$CO$_3$ | Pd(OAc)$_2$ | (t-Bu)$_2$PCy | tetraMeCyPrCO$_2$H | 120 | 5 | 45.5 | 32.5 | 19.1 | 0.0 | 2.8 | 41.6 |
| 6 | Xylene | K$_2$CO$_3$ | Pd(OAc)$_2$ | (t-Bu)$_2$PCy | (CH$_3$CH$_2$)$_2$CHCO$_2$H | 120 | 5 | 61.8 | 21.2 | 12.7 | 0.5 | 3.8 | 59.4 |
| 7 | Xylene | K$_2$CO$_3$ | Pd(OAc)$_2$ | (t-Bu)$_2$PCy | CyPnCO$_2$H | 120 | 5 | 52.0 | 28.2 | 18.7 | 0.0 | 1.1 | 46.8 |
| 8 | Xylene | K$_2$CO$_3$ | Pd(OAc)$_2$ | (t-Bu)$_2$PCy | 1-ad-CO$_2$H | 120 | 5 | 49.9 | 29.5 | 20.1 | 0.0 | 0.6 | 44.4 |
| 9 | Xylene | K$_2$CO$_3$ | Pd(OAc)$_2$ | (t-Bu)$_2$PCy | CyPenteneCO$_2$H | 120 | 5 | 37.0 | 37.1 | 25.7 | 0.0 | 0.3 | 31.8 |
| 10 | Xylene | K$_2$CO$_3$ | Pd(OAc)$_2$ | (t-Bu)$_2$PCy | 3-THFCO$_2$H | 120 | 5 | 50.5 | 29.0 | 20.1 | 0.0 | 0.3 | 44.9 |
| 11 | Xylene | K$_2$CO$_3$ | PdCl2 | (t-Bu)$_2$PCy | PivOH | 120 | 5 | 86.2 | 6.1 | 5.6 | 0.0 | 2.1 | 85.2 |

Abbreviations in the Table represent the following:
CyPrCO$_2$H: cyclopropanecarboxylic acid
tetraMeCyPrCO$_2$H: 2,2,3,3-tetramethylcyclopropanecarboxylic acid
CyPnCO$_2$H: cyclopentanecarboxylic acid
1-ad-CO$_2$H: 1-adamantanecarboxylic acid
CyPenteneCO$_2$H: 3-cyclopentenecarboxylic acid
3-THFCO$_2$H: tetrahydrofuran-3-carboxylic acid

INDUSTRIAL APPLICABILITY

The novel coupling process of the present invention, wherein a phenyl derivative represented by the formula (1) and a heterocyclic derivative represented by the formula (2) are coupled in the presence of a transition metal compound to obtain a phenyl-substituted heterocyclic derivative represented by the formula (3), is useful for producing a xanthine oxidase inhibitor, which is a therapeutic agent for hyperuricemia, or an intermediate thereof in a process involving a small number of steps and, consequently, in high yield and at low cost.

The invention claimed is:
1. A process comprising reacting a compound represented by the following formula (1):

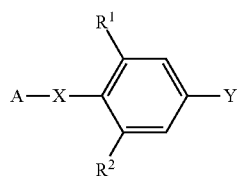

(1)

(In the formula (1), R$^1$ represents a hydrogen atom or halogen atom; R$^2$ represents a hydrogen atom, cyano group, nitro group, halogen atom, formyl group, or halomethyl group; A represents a hydrogen atom, C$_1$ to C$_8$ alkyl group, C$_3$ to C$_6$ cycloalkyl group, phenyl group, fluorine atom (only when X is a bond), or protecting group for a hydroxyl group (only when X is an oxygen atom), wherein A may be substituted by 1 to 3 substituents, such substituent representing a group selected from the group consisting of a halogen atom, C$_1$ to C$_4$ alkyl group, C$_1$ to C$_4$ alkoxy group, C$_1$ to C$_4$ alkylthio group, C$_3$ to C$_6$ cycloalkyl group, phenyl group, phenoxy group, and pyridyl group; X represents a bond (only when A is a phenyl group or fluorine atom) or oxygen atom; and Y represents a leaving group)
and a compound represented by the following formula (2):

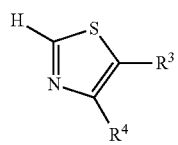

(2)

(In the formula (2), H represents a hydrogen atom; R$^3$ represents COOR$^{3a}$ or COR$^{3b}$; R$^{3a}$ represents a hydrogen atom, C$_1$ to C$_4$ alkyl group, or ester-type protecting group for a carboxyl group; R$^{3b}$ represents a amide-type protecting group for a carboxyl group, the protecting group forming an amide with a neighboring carbonyl group; R$^4$ represents a hydrogen atom, halogen atom, or C$_1$ to C$_4$ alkyl group);
in the presence of a transition metal compound selected from the group consisting of zero-valent palladium and a salt of mono- or di-valent palladium to produce a phenyl-substituted heterocyclic derivative represented by the following formula (3):

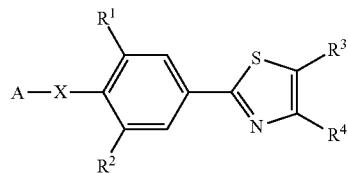

(3)

(in the formula (3), A, X, R$^1$, and R$^2$ are the same as defined in the formula (1); and R$^3$ and R$^4$ are the same as defined in the formula (2)).

2. The production process according to claim 1, wherein A is a C$_1$ to C$_5$ alkyl group.
3. The production process according to claim 1, wherein A is an isobutyl group.
4. The production process according to claim 1, wherein X is an oxygen atom.
5. The production process according to claim 1, wherein R$^1$ is a hydrogen atom.
6. The production process according to claim 1, wherein R$^2$ is a cyano group.
7. The production process according to claim 1, wherein Y represents a halogen atom, —OCO$_2$—(C$_1$ to C$_4$ alkyl group), —OCO$_2$-(phenyl group), —OSO$_2$—(C$_1$ to C$_4$ alkyl group), —OSO$_2$-(phenyl group), or a diazonium group wherein, in Y, the C$_1$ to C$_4$ alkyl group may be substituted with 1 to 3 halogen atoms and the phenyl group may be substituted with 1 to 3 halogen atoms or C$_1$ to C$_4$ alkyl groups.
8. The production process according to claim 1, wherein R$^4$ is a methyl group.
9. The production process according to claim 1, wherein the transition metal compound is palladium (II) acetate (Pd(OAc)$_2$), palladium (II) propionate (Pd(O(C=O)CH$_2$CH$_3$)$_2$), palladium (II) 2-methylpropanoate (Pd(O(C=O)CH(CH$_3$)$_2$)$_2$, palladium pivalate (Pd(OPiv)$_2$), palladium (II) chloride (PdCl$_2$), palladium (I) bromide (Pd$_2$Br$_2$), or palladium (II) hydroxide (Pd(OH)$_2$).
10. The production process according to claim 1, wherein the transition metal compound is palladium (II) acetate (Pd(OAc)$_2$), palladium (II) propionate (Pd(O(C=O)CH$_2$CH$_3$)$_2$), palladium (II) 2-methylpropanoate (Pd(O(C=O)CH(CH$_3$)$_2$)$_2$, or palladium pivalate (Pd(OPiv)$_2$).
11. The production process according to claim 1, wherein a ligand capable of coordinating to the transition metal compound is additionally present during the course of the reaction.
12. The production process according to claim 11, wherein the ligand is a phosphine-type ligand.
13. The production process according to claim 12, wherein the phosphine-type ligand is tri(tert-butyl)phosphine, di(tert-butyl)methylphosphine, tert-butyldicyclohexylphosphine, di(tert-butyl)cyclohexylphosphine, tri(cyclohexyl)phosphine, 2-dicyclohexylphosphino-2',6'-diisopropoxy-1,1'-biphenyl, 2-dicyclohexylphosphino-2',4',6'-triisopropyl-1,1'-biphenyl, or a salt thereof.

14. The production process according to claim 1, wherein a base is additionally present during the course of the reaction.

15. The production process according to claim 14, wherein the base is potassium carbonate, potassium bicarbonate, cesium carbonate, or tetra-n-butylammonium fluoride.

16. The production process according to claim 1, wherein a silver salt is additionally present during the course of the reaction.

17. The production process according to claim 16, wherein the silver salt is silver carbonate.

18. The production process according to claim 1, wherein a $C_1$ to $C_{12}$ carboxylic acid or salt thereof is additionally present during the course of the reaction.

19. The production process according to claim 18, wherein the carboxylic acid or salt thereof is 2-methylpropanoic acid, pivalic acid, or a salt thereof.

\* \* \* \* \*